(12) United States Patent
Combadiere et al.

(10) Patent No.: US 7,374,872 B2
(45) Date of Patent: May 20, 2008

(54) CC CHEMOKINE RECEPTOR 5 DNA, NEW ANIMAL MODELS AND THERAPEUTIC AGENTS FOR HIV INFECTION

(75) Inventors: Christophe Combadiere, Paris (FR); Philip M. Murphy, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 10 days.

(21) Appl. No.: 11/594,375

(22) Filed: Nov. 7, 2006

(65) Prior Publication Data

US 2007/0087990 A1 Apr. 19, 2007

Related U.S. Application Data

(60) Division of application No. 10/700,313, filed on Oct. 31, 2003, now Pat. No. 7,151,087, which is a continuation of application No. 08/864,458, filed on May 28, 1997, now abandoned.

(60) Provisional application No. 60/018,508, filed on May 28, 1996.

(51) Int. Cl.
C12Q 1/00 (2006.01)
(52) U.S. Cl. ......................................................... 435/4
(58) Field of Classification Search ...................... None
See application file for complete search history.

(56) References Cited

U.S. PATENT DOCUMENTS

| 5,440,021 | A | 8/1995 | Chuntharapai et al. |
|---|---|---|---|
| 5,939,320 | A | 8/1999 | Littman et al. |
| 6,025,154 | A | 2/2000 | Li et al. |
| 6,265,184 | B1 | 7/2001 | Gray et al. |
| 6,268,477 | B1 | 7/2001 | Gray et al. |
| 6,344,545 | B1 | 2/2002 | Allaway et al. |
| 6,448,375 | B1 | 9/2002 | Samson et al. |
| 6,511,826 | B2 | 1/2003 | Li et al. |
| 6,528,625 | B1 | 3/2003 | Wu et al. |
| 2001/0000241 | A1 | 4/2001 | Li et al. |
| 2002/0076745 | A1 | 6/2002 | Li et al. |
| 2002/0099176 | A1 | 7/2002 | Li et al. |
| 2002/0106742 | A1 | 8/2002 | Samson et al. |
| 2002/0110805 | A1 | 8/2002 | Samson et al. |
| 2002/0110870 | A1 | 8/2002 | Samson et al. |
| 2002/0132269 | A1 | 9/2002 | Li et al. |
| 2002/0150888 | A1 | 10/2002 | Gray et al. |
| 2003/0023044 | A1 | 1/2003 | Li et al. |

FOREIGN PATENT DOCUMENTS

| CA | 2146328 | 5/1994 |
|---|---|---|
| EP | 0 310 136 A2 | 4/1989 |
| WO | WO 94/12635 | 6/1994 |
| WO | WO 95/19436 | 7/1995 |
| WO | WO 96/39437 | 12/1996 |
| WO | WO 97/22698 | 6/1997 |
| WO | WO 97/32019 | 9/1997 |
| WO | WO 97/37005 | 10/1997 |
| WO | WO 97/44055 | 11/1997 |
| WO | WO 97/47318 | 12/1997 |

OTHER PUBLICATIONS

Samson et al., Molecular Cloning and Functional Expression of a New Human CC—Chemokine Receptor Gene, Biochemistry, Mar. 1996, 35:3362-3367.*
Alkhatib et al., "CC CKR5: A RANTES, MIP-1α, MIP-1β Receptor as a Fusion Cofactor for Macrophage-Tropic HIV-1," *Science*, 272:1955-1958, Jun. 28, 1996.
Arenzana-Selsdedos et al., "HIV blocked by chemokine antagonist," *Nature* 383:400, Oct. 3, 1996.
Aversa et al., "An Interleukin 4 (IL-4) Mutant Protein Inhibits both IL-4 or IL-13—induced Human Immunoglobulin G4 (IgG4) and IgE Synthesis and B Cell Proliferation: Support for a Common Component Shared by IL-4 and IL-13 Receptors," *J. Exp. Med.*, 178:2213-2218, Dec. 1993.
Carroll et al., "Differential Regulation of HIV-1 Fusion Cofactor Expression by CD28 Costimulation of CD4+ T Cells," *Science* 276:273-276, Apr. 11, 1997.
Choe et al., "The β-Chemokine Receptors CCR3 and CCR5 Facilitate Infection by Primary HIV-1 Isolates," *Cell* 85:1135-1148 (Jun. 28, 1996).
Cocchi et al., "Identification of RANTES, MIP-1α, and MIP-1β as the Major HIV-Suppressive Factors Produced by CD8+ T Cells," *Science*, 270: 1811-1815, Dec. 15, 1995.
Combadiere et al., "Cloning and Functional Expression of a Human Eosinophil CC Chemokine Receptor," *J. Biol. Chem.* 270:16491-16494 (1995).
Combadiere and Murphy, "Cloning and Functional Expression of a Human Monocyte CC Chemokine Receptor," *The American Society for Cell Biology*, Abstract; Submitted to 1995 Annual Meeting no later than Aug. 1, 1995.

(Continued)

*Primary Examiner*—Bruce R. Campell
*Assistant Examiner*—Nicole Kinsey White
(74) *Attorney, Agent, or Firm*—Klarquist Sparkman, LLP

(57) ABSTRACT

The susceptibility of human macrophages to human immunodeficiency virus (HIV) infection depends on cell surface expression of the human CD4 molecule and CC cytokine receptor 5. CCR5 is a member of the 7-transmembrane segment superfamily of G-protein-coupled cell surface molecules. CCR5 plays an essential role in the membrane fusion step of infection by some HIV isolates. The establishment of stable, nonhuman cell lines and transgenic mammals having cells that coexpress human CD4 and CCR5 provides valuable tools for the continuing research of HIV infection. In addition, antibodies which bind to CCR5, CCR5 variants, and CCR5-binding agents, capable of blocking membrane fusion between HIV and target cells represent potential anti-HIV therapeutics for macrophage-tropic strains of HIV.

9 Claims, 5 Drawing Sheets

OTHER PUBLICATIONS

Combadiere et al., "Cloning and functional expression of CC CKR5, a human monocyte CC chemokine receptor selective for MIP-1α, MIP-1β, and RANTES," *J. Leuk. Biol.* 60:147-152, Jul. 1996.

Combadiere and Murphy, "Cloning and Functional Expression of Two Human Monocyte CC Chemokine Receptors," *The American Society for Biochemistry and Molecular Biology*, Abstract, submitted to 1996 Annual Meeting no later than Jan. 30, 1996.

Combadiere et al., "Cloning, Chromosomal Localization, and RNA Expression of a Human β Chemokine Receptor-Like Gene," *DNA and Cell Biol.*, 14(8):673-680, Nov. 8, 1995.

Deng et al., "Identification of a major co-receptor for primary isolates of HIV-1," *Nature* 381:661-666 (Jun. 20, 1998).

Doranz et al., "A Dual-Tropic Primary HIV-1 Isolate That Uses Fusin and the β-Chemokine Receptors CKR-5, CKR-3, and CKR-2b as Fusion Cofactors," *Cell* 85:1149-1158 (Jun. 28, 1996).

Dragic et al., "HIV-1 entry into CD4+ cells is mediated by the chemokine receptor CC-CKR-5," *Nature* 381:-667-673 (Jun. 20, 1996).

Feng et al., "HIV-1 Entry Cofactor: Functional cDNA Cloning of a Seven-Transmembrane, G Protein—Coupled Receptor," *Science* 272:872-877 (1996).

Gong et al., "RANTES and MCP-3 Antagonists Bind Multiple Chemokine Receptors," *J. Biol. Chem.* 271:10521-10527 (1996).

He et al., "CCR3 and CCR5 are co-receptors for HIV-1 infection of microglia," *Nature* 385:645-649, Feb. 13, 1997.

Kaplan et al., "Chemokines and the allergic response," *Exp. Dermatol.*, 4(4 Pt 2):260-265, Aug. 1995 (Abstract Only).

Kern and Dietrich, "Eosinophil differentiating activity in sera of patients with AIDS under recombinant IL-2 substitution," *Blut* 52(4):249-254 (Apr. 1986) Abstract Only.

Kuhmann et al., "Frequent Substitution Polymorphisms in African Green Monkey CCR5 Cluster at Critical Sites for Infections by Simian Immunodeficiency Virus SIVagm, Implying Ancient Virus-Host Coevolution," *J Virology* 75(18):8449-8460 (Sep. 2001).

Mackewicz et al., "Role of β-Chemokines in Suppressing HIV Replication," *Science* 274:1393-1395 (Nov. 22, 1996).

Magnani et al., "The bone marrow in murine AIDS," *Br J Haematol.* 84(3):539-841 (Jul. 1993) Abstract Only.

Margolis et al., "Host vs. Viral Factors in Human Tissues Infected In Vitro with HIV-1," *Mol. Path. Model* Apr. 11, 1997.

McKenzie et al., "Interleukin 13, a T-cell-derived cytokine that regulates human monocyte and B-cell function," *Proc. Natl. Acad. Sci.* USA, 90:3735-3739, Apr. 1993.

Minty et al., "Interleukin-13 is a new human lymphokine regulating inflammatory and immune responses," *Nature*, 362:248-250, Mar. 18, 1993.

Raport et al. "Molecular Cloning and Functional Characterization of a Novel Human CC Chemokine Receptor (CCR5) for RANTES, MIP-1β, and MIP-1α," *J. Biol. Chem.*, 271(29):17161-17166, Jul. 19, 1996.

Robinson et al., "Chemokine expression in rheumatoid arthritis (RA): evidence of RANTES and macrophage inflammatory protein (MIP)-1 beta production by synovial T cells," *Clin. Exp. Immunol.*, 101(3):398-407, Sep. 1995 (Abstract Only).

Rucker et al., "Regions in β-Chemokine Receptors CCR5 and CCR2b that Determine HIV-1 Cofactor Specificity," *Cell* 87:437-446 (1996).

Samson et al., "Molecular Cloning and Functional Expression of a New Human CC—Chemokine Receptor Gene," *Biochem.*, 35(11):3362-3367, Mar. 1996.

Simmons et al., "Potent Inhibition of HIV-1 Infectivity in Macrophages and Lymphocytes by a Novel CCR5 Antagonist," *Science* 276:276-279, Apr. 11, 1997.

Uguccioni et al., "Actions of the chemotactic cytokines MCP-1, MCP-2, MCP-3, RANTES, MIP-1 alpha and MIP-1 beta on human monocytes," *Eur. J. Immunol.*, 25(1):64-68, Jan. 1995 (Abstract Only).

Zimmerman et al., "Inherited Resistance to HIV-1 Conferred by an Inactivating Mutation in CC Chemokine Receptor 5: Studies in Populations with Contrasting Clinical Phenotypes, Defined Racial Background, and Quantified Risk," *Mol. Med.* 3(1):23-36, Jan. 1997.

Zurawski et al., "Receptors for interleukin-13 and interleukin-4 are complex and share a novel component that functions in signal transduction," *EMBO J.*, 12(7):2663-2670, 1993.

Database PIR2 Accession No. G02653, Dec. 21, 1990 (also referred to as EMBL Accession No. A43113, Jul. 12, 1996).

* cited by examiner

FIG. 1A

```
gat ccg tcg acc gcc att atg gat gga tgg caa gaa act ctc ccc ggg      48
Asp Pro Ser Thr Ala Ile Met Asp Gly Trp Gln Glu Thr Leu Pro Gly
1               5                   10                  15 tgg aac aag atg gat tat caa gtg tca agt cca atc tat gac atc aat      96
Trp Asn Lys Met Asp Tyr Gln Val Ser Ser Pro Ile Tyr Asp Ile Asn
            20                  25                  30 tat tat aca tcg gag ccc tgc caa aaa atc aat gtg aag caa atc gca     144
Tyr Tyr Thr Ser Glu Pro Cys Gln Lys Ile Asn Val Lys Gln Ile Ala
        35                  40                  45 gcc cgc ctc ctg cct ccg ctc tac tca ctg gtg ttc atc ttt ggt ttt     192
Ala Arg Leu Leu Pro Pro Leu Tyr Ser Leu Val Phe Ile Phe Gly Phe
    50                  55                  60 gtg ggc aac atg ctg gtc atc ctc atc ctg ata aac tgc aaa agg ctg     240
Val Gly Asn Met Leu Val Ile Leu Ile Leu Ile Asn Cys Lys Arg Leu
65                  70                  75                  80 aag agc atg act gac atc tac ctg ctc aac ctg gcc atc tct gac ctg     288
Lys Ser Met Thr Asp Ile Tyr Leu Leu Asn Leu Ala Ile Ser Asp Leu
                85                  90                  95 ttt ttc ctt ctt act gtc ccc ttc tgg gct cac tac ttg gcc gcc cag     336
Phe Phe Leu Leu Thr Val Pro Phe Trp Ala His Tyr Leu Ala Ala Gln
            100                 105                 110 tgg gac ttt gga aat aca atg tgt caa ctc ttg aca ggg ctc tat ttt     384
Trp Asp Phe Gly Asn Thr Met Cys Gln Leu Leu Thr Gly Leu Tyr Phe
        115                 120                 125 ata ggc ttc ttc tct gga atc ttc ttc atc atc ctc ctg aca atc gat     432
Ile Gly Phe Phe Ser Gly Ile Phe Phe Ile Ile Leu Leu Thr Ile Asp
    130                 135                 140 agg tac ctg gct gtc gtc cat gct gtg ttt gct tta aaa gcc agg acg     480
Arg Tyr Leu Ala Val Val His Ala Val Phe Ala Leu Lys Ala Arg Thr
145                 150                 155                 160 gtc acc ttt ggg gtg gtg aca agt gtg atc act tgg gtg gtg gct gtg     528
Val Thr Phe Gly Val Val Thr Ser Val Ile Thr Trp Val Val Ala Val
                165                 170                 175 ttt gcg tct ctc cca gga atc atc ttt acc aga tct caa aaa gaa ggt     576
Phe Ala Ser Leu Pro Gly Ile Ile Phe Thr Arg Ser Gln Lys Glu Gly
            180                 185                 190 ctt cat tac acc tgc agc tct cat ttt cca tac agt cag tat caa ttc     624
Leu His Tyr Thr Cys Ser Ser His Phe Pro Tyr Ser Gln Tyr Gln Phe
        195                 200                 205 tgg aag aat ttc cag aca tta aag ata gtc atc ttg ggg ctg gtc ctg     672
Trp Lys Asn Phe Gln Thr Leu Lys Ile Val Ile Leu Gly Leu Val Leu
    210                 215                 220 ccg ctg ctt gtc atg gtc atc tgc tac tcg gga atc cta aaa act ctg     720
```

FIG. 1B

```
Pro Leu Leu Val Met Val Ile Cys Tyr Ser Gly Ile Leu Lys Thr Leu
225                 230                 235                 240 ctt cgg tgt cga aat gag aag aag agg cac agg gct gtg agg ctt atc      768
Leu Arg Cys Arg Asn Glu Lys Lys Arg His Arg Ala Val Arg Leu Ile
                245                 250                 255 ttc acc atc atg att gtt tat ttt ctc ttc tgg gct ccc tac aac att      816
Phe Thr Ile Met Ile Val Tyr Phe Leu Phe Trp Ala Pro Tyr Asn Ile
                260                 265                 270 gtc ctt ctc ctg aac acc ttc cag gaa ttc ttt ggc ctg aat aat tgc      864
Val Leu Leu Leu Asn Thr Phe Gln Glu Phe Phe Gly Leu Asn Asn Cys
            275                 280                 285 agt agc tct aac agg ttg gac caa gct atg cag gtg aca gag act ctt      912
Ser Ser Ser Asn Arg Leu Asp Gln Ala Met Gln Val Thr Glu Thr Leu
        290                 295                 300 ggg atg acg cac tgc tgc atc aac ccc atc atc tat gcc ttt gtc ggg      960
Gly Met Thr His Cys Cys Ile Asn Pro Ile Ile Tyr Ala Phe Val Gly
305                 310                 315                 320 gag aag ttc aga aac tac ctc tta gtc ttc ttc caa aag cac att gcc     1008
Glu Lys Phe Arg Asn Tyr Leu Leu Val Phe Phe Gln Lys His Ile Ala
                325                 330                 335 aaa cgc ttc tgc aaa tgc tgt tct att ttc cag caa gag gct ccc gag     1056
Lys Arg Phe Cys Lys Cys Cys Ser Ile Phe Gln Gln Glu Ala Pro Glu
                340                 345                 350 cga gca agc tca gtt tac acc cga tcc act ggg gag cag gaa ata tct     1104
Arg Ala Ser Ser Val Tyr Thr Arg Ser Thr Gly Glu Gln Glu Ile Ser
            355                 360                 365 gtg ggc ttg tga cac gga ctc aag tgg gct ggt gac cca gtc aga gtt     1152
Val Gly Leu     His Gly Leu Lys Trp Ala Gly Asp Pro Val Arg Val
        370             375                 380 gtg cac atg gct tag ttt tca tac aca gcc tgg gct ggg ggt ggg gtg     1200
Val His Met Ala     Phe Ser Tyr Thr Ala Trp Ala Gly Gly Gly Val
        385             390                 395 gga gag gtc ttt ttt aaa agg aag tta ctg tta tag agg gtc taa gat     1248
Gly Glu Val Phe Phe Lys Arg Lys Leu Leu Leu     Arg Val     Asp
        400                 405                 410 tca tcc at                                                           1256
```

SEQ ID NO: 3

```
aagaaactct ccccgggtgg aacaag atg gat tat caa gtg tca agt cca atc      53
tat gac atc aat tat tat aca tcg gag ccc tgc caa aaa atc aat gtg      101
aag caa atc gca gcc cgc ctc ctg cct ccg ctc tac tca ctg gtg ttc      149
atc ttt ggt ttt gtg ggc aac atg ctg gtc atc ctc atc ctg ata aac      197
tgc aaa agg ctg aag agc atg act gac atc tac ctg ctc aac ctg gcc      245
atc tct gac ctg ttt ttc ctt ctt act gtc ccc ttc tgg gct cac tat      293
gct gcc gcc cag tgg gac ttt gga aat aca atg tgt caa ctc ttg aca      341
ggg ctc tat ttt ata ggc ttc ttc tct gga atc ttc ttc atc atc ctc      389
ctg aca atc gat agg tac ctg gct gtc gtc cat gct gtg ttt gct tta      437
aaa gcc agg acg tca acc ttt ggg gtg gtg aca agt gtg atc act tgg      485
gtg gtg gct gtg ttt gcg tct ctc cca gga atc atc ttt acc aga tct      533
caa aaa gaa ggt ctt cat tac acc tgc agc tct cat ttt cca tac agt      581
cag tat caa ttc tgg aag aat ttc cag aca tta aag ata gtc atc ttg      629
ggg ctg gtc ctg ccg ctg ctt gtc atg gtc atc tgc tac tcg gga atc      677
cta aaa act ctg ctt cgg tgt cga aat gag aag aag agg cac agg gct      725
gtg agg ctt atc ttc acc atc atg att gtt tat ttc ctc ttc tgg gct      773
ccc tac aac att gtc ctt ctc ctg aac acc ttc cag gaa tcc ttt ggc      821
ctg aat aat tgc agt agc tct aac agg ttg gac caa gct atg cag gtg      869
aca gag act ctt ggg atg acg cac tgc tgc atc aac ccc atc atc tat      917
gcc ttt gtc ggg gag aag ttc aga aac tac ctc tta gtc ttc ttc caa      965
aag cac att gcc aaa cgc ttc tgc aaa tgc tgt tct att ttc cag caa     1013
gag gct ccc gag cga gca agc tca gtt tac acc cga tcc act ggg gag     1061
cag gaa ata tct gtg ggc ttg tgacacggac tcaagtgggc tggtgaccca        1112
gtcagagttg tgcacatggc ttagttttca tacacagcct gggctggggg tggggtggga     1172
gaggtctttt ttaaaaggaa gttactgtta tagagggtct aagattcatc cat          1225
```

SEQ ID NO : 4

```
MDYQVSSPIYDINYYTSEPCQKINVKQIAARLLPPLYSLVFIFG
FVGNMLVILILINCKRLKSMTDIYLLNLAISDLFFLLTVPFWAHYAAAQWDFGNTMCQ
LLTGLYFIGFFSGIFFIILLTIDRYLAVVHAVFALKARTVTFGVVTSVITWVVAVFAS
LPGIIFTRSQKEGLHYTCSSHFPYSQYQFWKNFQTLKIVILGLVLPLLVMVICYSGIL
KTLLRCRNEKKRHRAVRLIFTIMIVYFLFWAPYNIVLLLNTFQEFFGLNNCSSSNRLD
QAMQVTETLGMTHCCINPIIYAFVGEKFRNYLLVFFQKHIAKRFCKCCSIFQQEAPER
ASSVYTRSTGEQEISVGL
```

CC CHEMOKINE RECEPTOR 5 DNA, NEW ANIMAL MODELS AND THERAPEUTIC AGENTS FOR HIV INFECTION

This is a divisional of U.S. patent application Ser. No. 10/700,313, filed Oct. 31, 2003, now U.S. Pat. No. 7,151,087, which is a continuation of U.S. patent application Ser. No. 08/864,458 (abandoned), filed May 28, 1997, which in turn claims the benefit of U.S. Provisional Application 60/018,508, filed May 28, 1996. All applications are incorporated herein in their entirety.

FIELD OF THE INVENTION

The present invention relates to in vitro and in vivo models for the study of human immunodeficiency virus (HIV) infection and the effectiveness of anti-HIV therapeutics. The invention more specifically relates to cell surface proteins that participate in HIV infection and which are useful for the development of animal models.

BACKGROUND OF THE INVENTION

An HIV infection cycle begins with the entry of an HIV virus into a target cell. Entry commences when an HIV envelope glycoprotein (env) binds to a human CD4 molecule in a target cell membrane. This binding leads to fusion of virus and cell membranes, which in turn facilitates virus entry into the host. The HIV-infected host cell eventually expresses env on its surface. This expression allows the infected cell to fuse with uninfected, CD4-positive cells, thereby spreading the virus.

Recent studies have shown that the HIV fusion process occurs with a wide range of human cell types that either express human CD4 endogenously or that have been engineered to express human CD4. The fusion process, however, does not occur with nonhuman cell types engineered to express human CD4 even though these nonhuman cells still can bind env. The disparity between human and nonhuman cell types exists because membrane fusion requires the coexpression of human CD4 and one or more cofactors specific to human cell types. Nonhuman cell types that have been engineered to express human CD4 but not the additionally required factor(s) are incapable of membrane fusion, and therefore are nonpermissive for HIV infection.

Some individual HIV isolates, designated "macrophage-tropic," efficiently infect primary macrophages but not immortalized T-cell lines. Other isolates, designated "T-cell line-tropic," have the opposite property and infect immortalized T-cell lines more efficiently than they infect primary macrophages. Both types of isolates readily infect primary T-cells from the body, however. The selective tropism of these two types of isolates is thought to be due to their requirements for distinct cofactors that are differentially expressed on different CD4 positive cell types. It should be understood that other HIV strains are "dual-tropic" and have the ability to infect both macrophages and immortalized T-cell lines and are believed to be able to use more than one cofactor.

Recently a cofactor required for fusion of virus and cell membranes has been described. Feng et al., *Science* 272: 872-7 (1996). This factor, called "fusin," (also known as CXCR4) permits cells that contain human CD4 to fuse with the surface of an HIV virus. Fusin functions preferentially for T-cell line-tropic HIV-1 isolates and much less well for macrophage-tropic HIV-1 isolates.

The discovery of fusin allows the creation of a successful small animal model. Such a model is crucial for studies of HIV infection and of the effectiveness of anti-HIV therapeutics. But the presence of fusin enables the study of T-cell line-tropic but not macrophage-tropic isolates. This is an important distinction because macrophage-tropic isolates represent the predominant type of isolates obtained from infected individuals. Macrophage-tropic isolates also appear to be preferentially transmitted between individuals. A putative cofactor that is necessarily expressed with CD4 to allow entry of macrophage-tropic isolates remains unknown.

In recent years, researchers have bred transgenic animals that contain cells which express human CD4 and which could be used as models for HIV infection of macrophages if the macrophage-specific factor were known. See, for example, Dunn et al., *Human immunodeficiency virus type 1 infection of human CD4-transgenic rabbits*, J. Gen. Vir. 76:1327-1336 (1995); Snyder et al., *Development and Tissue-Specific Expression of Human CD4 in Transgenic Rabbits*, Mol. Reprod. & Devel. 40:419428 (1995); Killeen et al., *Regulated Expression of Human CD4 Rescues Helper T-Cell Development in Mice Lacking Expression of Endogenous CD4*, EMBO J. 12:1547-1553 (1993); Forte et al., *Human CD4 Produced in Lymphoid Cells of Transgenic Mice Binds HIV gp120 and Modifies the Subsets of Mouse T-Cell Populations*, Immunogenetics 38:455-459 (1993).

A goal of research in this field is to find a putative factor for the macrophage-tropic isolates that could be co-expressed with CD4 in a small animal. Such co-expression would provide an animal model to develop efficacious therapies to combat infection by macrophage-tropic HIV isolates. The discovery of other essential cofactors would provide new targets for development of anti-HIV therapies.

SUMMARY OF THE INVENTION

The present invention is based on the discovery of a new CC chemokine receptor protein associated with HIV infection (formerly referred to as "CC CKR5", now more commonly known as "CCR5"). The invention provides isolated polynucleotides and polypeptides encoded by CCR5 polynucleotides, as well as antibodies directed against regions of CCR5 and peptide fragments of CCR5 which block HIV interaction with the CC CKR5 receptor.

It is an object of the present invention to provide therapeutic and preventative medicinal agents effective against HIV infection and effective in regulating monocyte accumulation and activation. In accomplishing these and other objects, there has been provided, in accordance with one aspect of the present invention a stable, nonhuman cell line, the cells of which contain DNA encoding CCR5. In accordance with another aspect of the invention a transgenic non-human mammal is provided comprised of cells that coexpress human CD4 and CCR5.

In another aspect of the invention, the invention provides an antibody which binds to CCR5 and which blocks membrane fusion between HIV and a target cell. In accordance with another aspect of the invention, there is provided a cell that expresses a CCR5 gene, wherein the CCR5 gene is not stably integrated into the genome of said cell.

In accordance with yet another aspect of the invention an isolated and purified peptide fragment of CCR5 is provided that blocks membrane fusion between HIV and a target cell.

In yet another aspect, the invention provides a method for identifying a compound which blocks membrane fusion between HIV and a CCR5 target cell or between an HIV-infected cell and a CCR5 positive uninfected cell. The method includes the steps of: a) incubating components comprising the compound and a CDU and CCR5 positive cell under conditions sufficient to allow the components to interact; b) contacting the components of step a) with HIV or an HIV-infected cell; and c) measuring the ability of the compound to block membrane fusion between HIV and the CCR5 positive cell or between an HIV-infected cell and a CCR5 positive uninfected cell.

In accordance with yet another aspect of the invention a method of inhibiting CCRS expression in a cell is provided, comprising introducing into the cell at least one antisense polynucleotide that causes the inhibition of CCR5 in the cell.

In accordance with yet another aspect of the invention is provided a CCR5-binding agent, wherein said agent blocks binding of a chemokine and HIV to CCR5.

The antibodies and blocking agents of the invention are also useful for providing methods for modulating an immune response in which macrophages are involved. For example, administration of CCR5 agonists or antagonists would be useful for modulating the immune response.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A shows an alignment of amino acid sequences deduced from cDNAs for CC CKR1 (SEQ ID NO: 9), CC CKR2B (SEQ ID NO: 8), and for CCR5 (SEQ ID NO: 4). Arabic numbers enumerate a CCR5 amino acid sequence (SEQ ID NO:4) and a variant with residue changed from alanine to leucine (SEQ ID NO: 2) that has been deduced from a CCR5 DNA sequence (SEQ ID NO:3 and SEQ ID NO: 1, respectively) and are left-justified. Putative membrane-spanning segments I-VII are noted. Vertical bars show identities between adjacent residues and open boxes show predicted sites for N-linked glycosylation. Dashes and gaps have been inserted to optimize the alignments. Extracellular portions of the CCR5 polypeptide are located between transmembrane domains 2 and 3, transmembrane domains 4 and 5, transmembrane domains 6 and 7, and in the amino terminal segment before transmembrane domain 1.

FIGS. 1B and 1C show the nucleotide and deduced amino acid sequence (SEQ ID NO:11) for a CCR5 variant where nucleotides 293-296 of the wild-type DNA is changed from CTTG to TGCT resulting in a change at amino acid residue 127, from Alanine to Leucine. The translated protein is shown in SEQ ID NO: 2 (and the corresponding cDNA in SEQ ID NO: 1).

FIG. 1D shows the nucleotide and deduced amino acid sequence (SEQ ID NO:3 and 4, respectively) for CCR5.

DETAILED DESCRIPTION OF PREFERRED EMBODIMENTS

Figure 2:
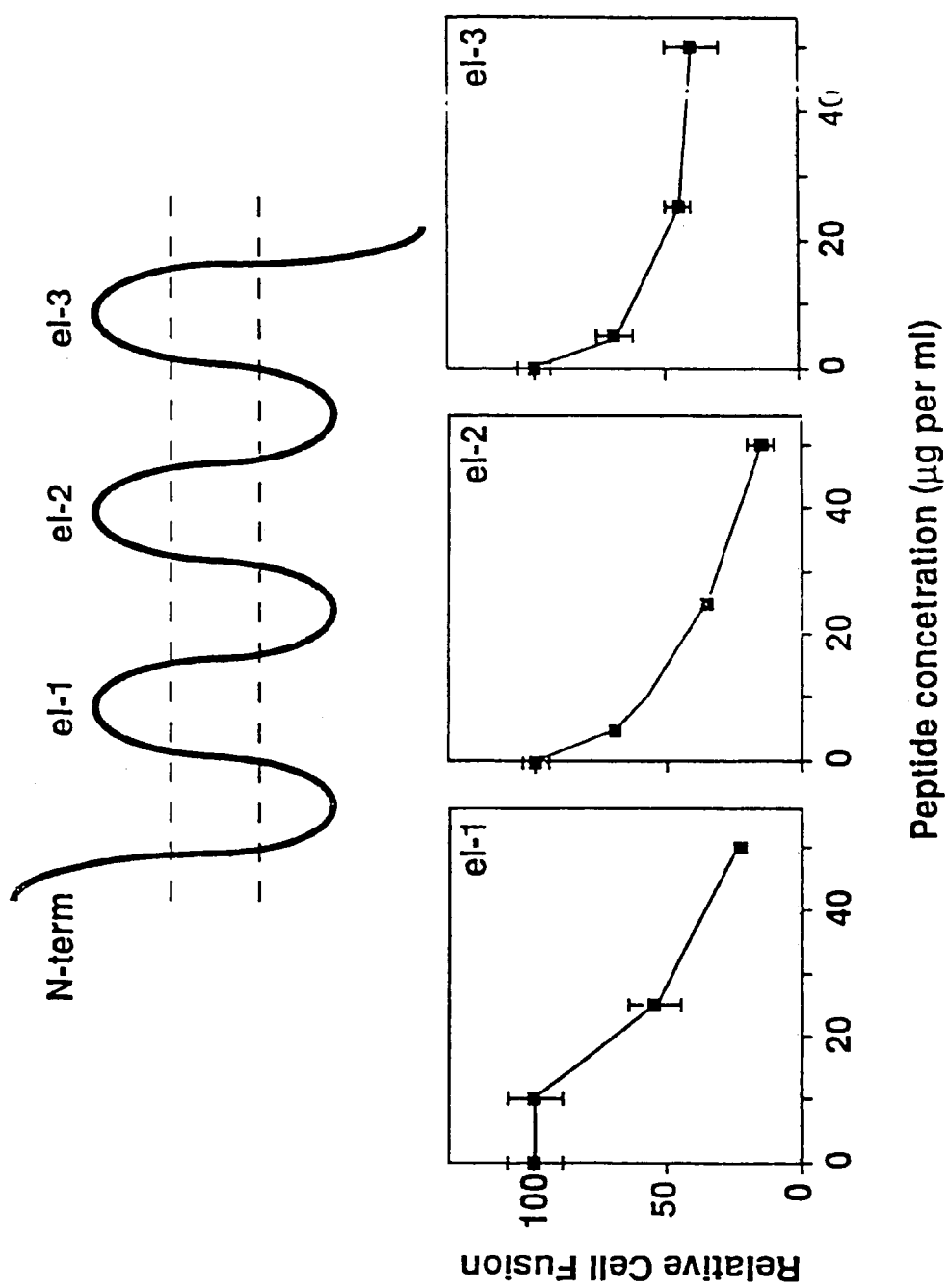
FIG. 2 shows CCR5 peptides which inhibit fusion between cells expressing the HIV-1 Env from the macrophage-tropic Ba-L isolate and murine cells co-expressing CD4 and CCR5. Peptides were preincubated with HIV-Env-expressing cells for 1 hour at a concentration from 0-50 μg/ml before mixing with cells which express CD4 and CCR5.

The present invention originated from studies on receptor proteins of chemokines. The inventors cloned, sequenced, and functionally expressed a human cDNA encoding a novel macrophage-selective CC chemokine receptor that has been designated CCR5.

During their investigation, the inventors discovered that CCR5 is a necessary cofactor for infection by macrophage-tropic HIV isolates. More particularly, the inventors found that when they transgenically expressed human CCR5 in non-human cells which also transgenically express human CD4, the altered cells could fuse with cells that express the env envelope protein from macrophage-tropic strains of HIV. It should be understood that other HIV strains are "dual-tropic" and have the ability to infect both macrophages and immortalized T-cell lines and are believed to be able to use more than one cofactor. Furthermore, the inventors reasoned that antibodies against CCR5 can inhibit the fusion of cells that contain CD4 and CCR5, upon contact with cells that express the env protein from macrophage-tropic strans of HIV. Antibodies which bind CCR5 can inhibit infection of cells that contain CCR5 and CD4 by macrophage-tropic strains of HIV. The insights of the present invention enable the development of new tools to study HIV infection of macrophages and the discovery of new HIV treatment methodologies based on chemokine receptor biochemistry.

Chemokine receptors are thought to have seven trans-membrane-domains, are coupled to G-protein and participate in cellular responses to chemokines. Receptor CCR5 that has been cloned by the inventors is the fifth human CC chemokine receptor identified to date. The five receptors bind overlapping but distinct subsets of CC chemokines. Of the five, only CC chemokine receptor 5 ("CCR5") displays a CC chemokine specificity profile that matches the profile for suppression of HIV-1 infection. Cocchi et al., Science 270, 1811 (1995). RANTES, MIP-1α and MIP-1β are potent agonists of CCR5, but MCP-1 and MCP-3 are not, as summarized by Combadiere et al. in *J. Biol. Chem.* 270: 16491-4 (1995), *J. Biol. Chem.* 270: 30235 (1995), and *Molec. Biol. Cell.* 6: 224a (1995) and by Samson et al. in *Biochemistry* 35: 3362 (1996) the disclosures of which are incorporated herein in their entireties.

Isolation of cDNA Encoding CCR5

The gene for the chemokine receptor of the present invention can be cloned from a human cDNA library. Methods used to clone novel chemokine receptor-like cDNAs from a λgt11 cDNA library made from peripheral blood mononuclear cells of a patient with eosinophilic leukemia have been described by Combadiere et al., *DNA Cell Biol.* 14: 673-80 (1995), which is herein incorporated in its entirety by reference. A cDNA encoding CCR5 also can be isolated by the procedure described by U.S. provisional patent application 60/010,854 filed on Jan. 30, 1996, which is herein incorporated by reference.

The above-described methods can be used to identify DNA sequences that code for one or more CCR5 polypeptide sequences. A nucleotide sequence determined by the inventors, herein described as SEQ ID NO:3 of the present invention, has been deposited with the Genbank/EMBL data libraries under accession number U57840. But many other related sequences that code for CCR5 and altered forms of CCR5 are contemplated in context of the various embodiments enumerated herein (e.g., SEQ ID NO:1).

In preferred embodiments fusion between env-expressing effector cells and CD4-expressing and CCR5-expressing target cells, prepared by infection with vaccinia virus, induces activation of *Escherichia coli* lacZ, causing β-galactosidase production in fused cells as described by Nussbaum et al., *J. Virol.* 68: 5411 (1994), which is incorporated in its entirety by reference. The specificity of cell fusion as measured with this assay is equivalent to the specificity of infection by HIV-1 virions.

The invention provides an isolated polynucleotide sequence encoding a polypeptide having an amino acid sequence as set forth in SEQ ID NO:4. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode CCR5. It is understood that all polynucleotides encoding all or a portion of CCR5 are also included herein, as long as they encode a polypeptide with CCR5 activity (e.g., act as a cofactor for HIV infection). Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, CCR5 polynucleotide may be subjected to site-directed mutagenesis. The polynucleotide sequence for CCR5 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of CCR5 polypeptide encoded by the nucleotide sequence is functionally unchanged. Also included are nucleotide sequences which encode CCR5 polypeptide, such as SEQ ID NO:1. In addition, the invention also includes a polynucleotide encoding a polypeptide having the biological activity of an amino acid sequence of SEQ ID NO:4 and having at least one epitope for an antibody immunoreactive with CCR5 polypeptide. Assays provided herein which show association between HIV infection and expression of CCR5 can be used to detect CCR5 activity.

Figure 1A:
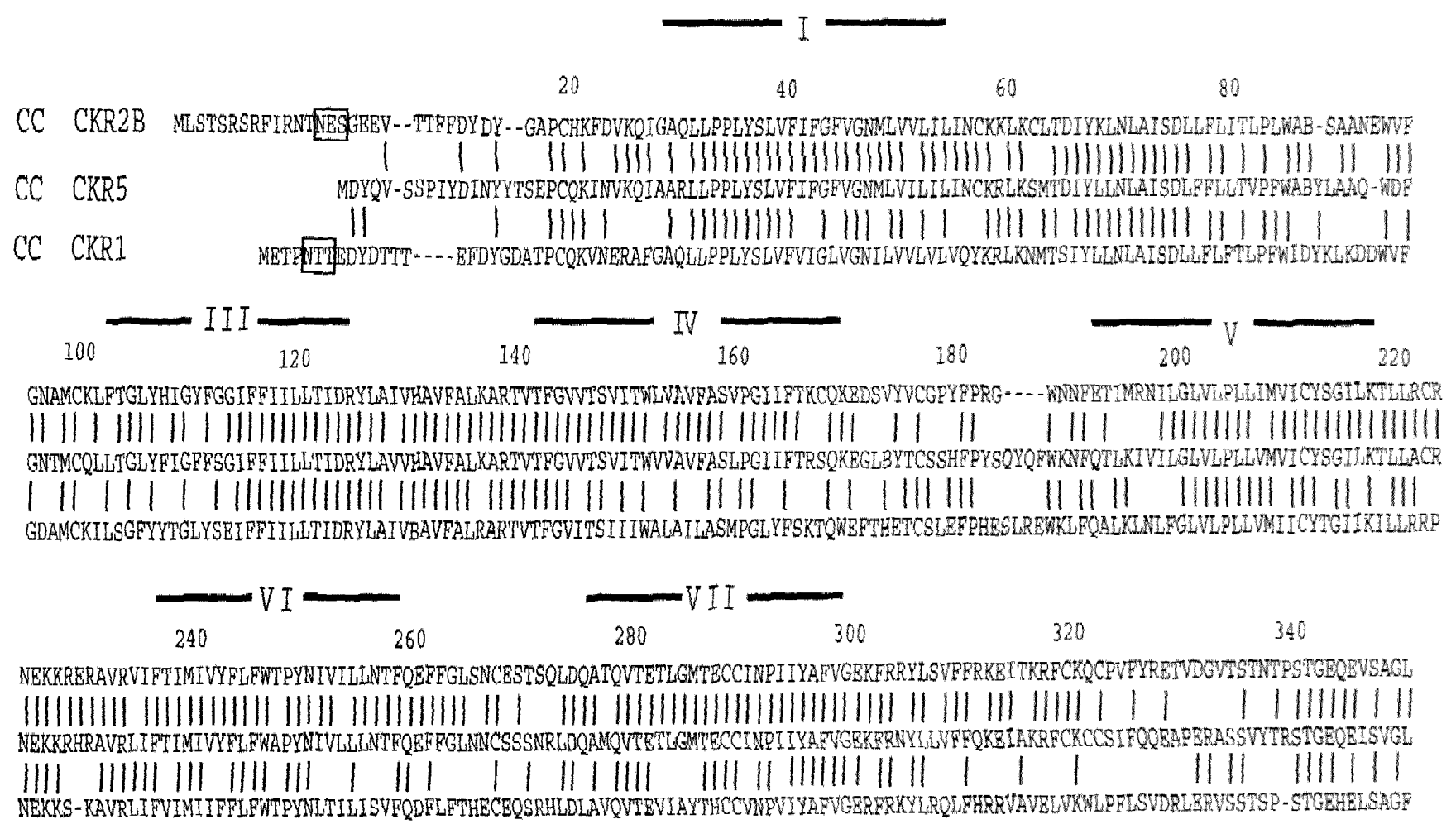

The polynucleotide encoding CCR5 includes the nucleotide sequence in FIG. 1 (SEQ ID NO:1 and 3), as well as nucleic acid sequences complementary to that sequence. A complementary sequence may include an antisense nucleotide. When the sequence is RNA, the deoxyribonucleotides A, G, C, and T of FIG. 1 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 1 (e.g., SEQ ID NO: 4). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Specifically disclosed herein is a cDNA sequence for CCR5. SEQ ID NO:3 represents the wild-type sequence and SEQ ID NO:1 represents a cDNA which encodes CCR5 having a conservative substitution of Leucine for Alanine at amino acid residue 127. The result of this conservative variation should not affect biological activity of CCR5 polypeptide or peptides containing the variation (see Example 5).

DNA sequences of the invention can be obtained by several methods. For example, the DNA can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Preferably the CCR5 polynucleotide of the invention is derived from a mammalian organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981). Alternatively, a subtractive library, as illustrated herein is useful for elimination of non-specific cDNA clones.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for CCR5 peptides having at least one epitope, using antibodies specific for CCR5. Such antibodies can be either polyclonally or monoclonally derived and used to detect expression product indicative of the presence of CCR5 cDNA.

Alterations in CCR5 nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example.

DNA sequences encoding CCR5 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the CCR5 polynucleotide sequences may be inserted into a recombinant expression vector. The term "recombinant expression vector" refers to a plasmid, virus or other vehicle known in the art that has been manipulated by insertion or incorporation of the CCR5 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g, T7, metallothionein I, or polyhedrin promoters).

Polynucleotide sequences encoding CCR5 can be expressed in either prokaryotes or eukaryotes. Hosts can include microbial, yeast, insect and mammalian organisms. However, since mature CCR5 is glycosylated, the choice of host cells depends on whether or not the glycosylated or non-glycosylated form of CCR5 is desired. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the CCR5 coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized to express the CCR5 coding sequence. These include but are not limited to microorganisms such as bacteria transformed with recombinant bacteriophage DNA, plasmid DNA or cosmid DNA expression vectors containing the CCR5 coding sequence; yeast transformed with recombinant yeast expression vectors containing the CCR5 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CCR5 coding sequence; insect cell systems infected with recombinant virus expression vectors (e.g., baculovirus) containing the CCR5 coding sequence; or animal cell systems infected with recombinant virus expression vectors (e.g., retroviruses, adenovirus, vaccinia virus) containing the CCR5 coding sequence, or transformed animal cell systems engineered for stable expression. Since CCR5 has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516-544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted CCR5 coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad.

Press, N.Y., Vol. 152, pp. 673-684; and The Molecular Biology of the Yeast *Saccharomyces,* 1982, Eds. Strathem et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. DM Glover, 1986, IRL Press, Wash., D.C.). Alternatively, vectors may be used which promote integration of foreign DNA sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, plasma membrane insertion of the gene product may be used as host cells for the expression of CCR5.

Mammalian cell systems which utilize recombinant viruses or viral elements to direct expression may be engineered. For example, when using adenovirus expression vectors, the. CCR5 coding sequence may be ligated to an adenovirus transcription/translation control complex, e.g., the late promoter and tripartite leader sequence. Alternatively, the vaccinia virus 7.5K promoter may be used. (e.g., see, Mackett et al., 1982, Proc. Natl. Acad. Sci. USA 79: 7415-7419; Mackett et al., 1984, J. Virol. 49: 857-864; Panicali et al., 1982, Proc. Natl. Acad. Sci. USA 79: 4927-4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the CCR5 gene in host cells (Cone & Mulligan, 1984, *Proc. Natl. Acad. Sci. USA* 81:6349-6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the CCR5 cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 12 days in an enriched media, and then are switched to a selective media. A number of selection systems may be used, including but not limited to the herpes simplex virus thymidine kinase (Wigler et al., 1977, *Cell* 11: 223), hypoxanthine-guanine phosphoribosyltransferase (Szybalska & Szybalski, 1962, *Proc. Natl. Acad. Sci. USA* 48: 2026), and adenine phosplioribosyltranslerase (Lowy et al., 1980, *Cell* 22: 817) genes can be employed in tk, hgprt⁻ or aprt⁻ cells respectively. Also, antimetabolite resistance can he used as the basis of selection for dhfr, which confers resistance to methotrexate (Wigler et al., 1980, *Proc. Natl. Acad. Sci. USA* 77:3567; O'Hare et al. 1981, *Proc Natl. Acad. Sci. USA* 78: 1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85: 8047); and ODC (ornithine decarboxylase) which confers resistance to the ornithine decarboxylase inhibitor, 2-(difluoromethyl)-DL-omithine, DFMO (McConlogue L., 1987, In: Current Communications in Molecular Biology, Cold Spring harbor Laboratory ed.).

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the CCR5 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Cell Lines

In one embodiment, the present invention relates to stable recombinant cell lines, the cells of which express CCR5 polypeptide or coexpress human CD4 and CCR5 and contain DNA that encodes CCR5. Suitable cell types include but are not limited to cells of the following types: NIH 3T3 (Murine), Mv 1 lu (Mink), BS-C-1 (African Green Monkey) and human embryonic kidney (HEK) 293 cells. Such cells are described, for example, in the Cell Line Catalog of the American Type Culture Collection (ATCC). These cells can be stably transformed by a method known to the skilled artisan. See, for example, Ausubel et al., *Introduction of DNA Into Mammalian Cells*, in CURRENT PROTOCOLS IN MOLECULAR BIOLOGY, sections 9.5.1-9.5.6 (John Wiley & Sons, Inc. 1995). "Stable" transformation in the context of the invention means that the cells are immortal to the extent of having gone through at least 50 divisions.

CCR5 can be expressed using inducible or constituitive regulatory elements for such expression. Commonly used constituitive or inducible promoters, for example, are known in the art. The desired protein encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the desired molecule may occur through the transient expression of the introduced sequence. Alternatively, permanent expression may occur through the integration of the introduced sequence into the host chromosome. Therefore the cells can be transformed stably or transiently.

An example of a vector that may be employed is one which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector, the number of copies of the vector which are desired in a particular host; and whether it is desirable to be able to "shuttle" the vector between host cells of different species.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors include vaccinia virus expression vectors. A third class of vectors relies upon the integration of the desired gene sequences into the host chromosome. Cells which have stably integrated the introduced DNA into their chromosomes may be selected by also introducing one or more markers (e.g., an exogenous gene) which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same-cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., Mol. Cell. Biol., 3:280 (1983), and others.

Once the vector or DNA sequence containing the construct has been prepared for expression, the DNA construct may be introduced (transformed) into an appropriate host. Various techniques may be employed, such as protoplast fusion, calcium phosphate precipitation, electroporation or other conventional techniques.

Transgenic Animals

In another embodiment, the present invention relates to transgenic animals having cells that coexpress human CD4 and CCR5. Such transgenic animals represent a model system for the study of HIV infection and the development of more effective anti-HIV therapeutics.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

It is highly preferred that the transgenic animals of the present invention be produced by introducing into single cell embryos DNA encoding CCR5 and DNA encoding human CD4, in a manner such that these polynucleotides are stably integrated into the DNA of germ line cells of the mature animal and inherited in normal mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo.

In a most preferred method the appropriate DNAs are coinjected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., MANIPULATING THE MOUSE EMBRYO (Cold Spring Harbor Press 1986); Krimpenfort et al., Bio/Technology 9:86 (1991); Palmiter et al., Cell 41:343 (1985); Kraemer et al., GENETIC MANIPULATION OF THE EARLY MAMMALIAN EMBRYO (Cold Spring Harbor Laboratory Press 1985); Hammer et al., Nature, 315:680 (1985); Purcel et al., Science, 244:1281 (1986); Wagner et al., U.S. Pat. No. 5,175,385; Krimpenfort et al., U.S. Pat. No.5,175,384, the respective contents of which are incorporated by reference.

The cDNA that encodes CCR5 can be fused in proper reading frame under the transcriptional and translational control of a vector to produce a genetic construct that is then amplified, for example, by preparation in a bacterial vector, according to conventional methods. See, for example, the standard work: Sambrook et al., MOLECULAR CLONING: A LABORATORY MANUAL (Cold Spring Harbor Press 1989), the contents of which are incorporated by reference. The amplified construct is thereafter excised from the vector and purified for use in producing transgenic animals.

Production of transgenic animals containing the gene for human CD4 have been described. See Snyder et al., supra; Dunn et al., supra, the contents of which are incorporated by reference.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional. by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a modified CCR5 coding sequence. In a preferred embodiment, the CCR5 gene is disrupted by homologous targeting in embryonic stem cells. For example, the entire mature C-terminal region of the CCR5 gene may be deleted as described in the examples below. Optionally, the CCR5 disruption or deletion may be accompanied by insertion of or replacement with other DNA sequences, such as a non-functional CCR5 sequence. In other embodiments, the transgene comprises DNA antisense to the coding sequence for CCR5. In another embodiment, the transgene comprises DNA encoding an antibody or receptor peptide sequence which is able to bind to CCR5. Where appropriate, DNA sequences that encode proteins having CCR5 activity but differ in nucleic acid sequence due to the degeneracy of the genetic code may also be used herein, as may truncated forms, allelic variants and interspecies homologues.

Antibodies Which Bind to CCR5 Inhibit Fusion

In another embodiment, the present invention relates to antibodies that bind CCR5 that block env-mediated membrane fusion (i) associated with HIV entry into a human CD4-positive target cell or (ii) between an HIV-infected cell and an uninfected human CD4-positive target cell. The invention also includes antibodies that bind to CCR5 and inhibit chemokine binding. For example, such antibodies may be useful for ameliorating immune response disorders associated with macrophages. Antibodies of the invention may also inhibit gp120 binding to CCR5. Such antibodies could represent research and diagnostic tools in the study of HIV infection and the development of more effective anti-HIV therapeutics. In addition, pharmaceutical compositions comprising antibodies against CCR5 may represent effective anti-HIV therapeutics.

An antibody suitable for blocking env-mediated membrane fusion, inhibiting chemokine binding, or blocking gp120 binding to CCR5, is specific for at least one portion of an extracellular region of the CCR5 polypeptide, as shown in FIG. 1 (SEQ ID NO:2 and 4). For example, one of skill in the art can use the peptides in SEQ ID NO:5-7 or other extracellular amino acids of CCR5 to generate appropriate antibodies of the invention. Alternatively, one of skill in the art can use whole cells expressing CCR5 as an immunogen for generation of anti-CCR5 antibodies which either block env-mediated membrane fusion, inhibit chemokine binding or block gp120 binding to CCR5. Anti-CCR5 antibodies of the invention may have any or all of these functions.

A target cell includes but is not limited to a cell of the following types: Mv 1 lu, NIH 3T3, BS-C-1, HEK293 cells and primary human T-cells and macrophages. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera*, in IMMUNOCHEMICAL PROTOCOLS (Manson, ed.), pages 1-5 (Humana Press 1992); Coligan et al., *Production of Polyclonal Antisera in Rabbits, Rats, Mice and Hamsters*, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al, sections 2.5.1-2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice With a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al, sections 2.7.1-2.7.12 and sections 2.9.1-2.9.3; Barnes et al, *Purification of Immunoglobulin G (IgG)*, in METHODS IN MOLECULAR BIOLOGY, VOL. 10, pages 79-104 (Humana Press 1992).

Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present. invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer* 46:310 (1990), which are hereby incorporated by reference.

Alternatively, a theapeutically useful anti-CCR5 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989), which is hereby incorporated in its entirety by reference. Techniques for producing humanized monoclonal antibodies are described, for example, by Jones et al., *Nature* 321: 522 (1986); Riechmann et al., *Nature* 332: 323 (1988); Verhoeyen et al., *Science* 239: 1534 (1988); Carter et al., *Proc. Nat'l Acad. Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No.4,331,647, and references contained therein. These patents are hereby incorporated in their entireties by reference. See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., *Science* 242: 423426 (1988); Ladner et al., U.S. Pat. No. 4,946,778; Pack et al., *Bio/Technology* 11: 1271 77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al. METHODS: A COMPANION TO METHODS IN ENZYMOLOGY, VOL. 2, page 106 (1991).

Antibodies that bind to CXCR4 chemokine receptor, another HIV fusion cofactor receptor, have been shown to block fusion of HIV strains that use CXCR4 receptor for infection (Feng, et al., *Science* 272:872, 1996; Endres, et al., *Cell* 87:745, 1996).

Variants of CCR5

The term "CCR5 variant" as used herein means a molecule that simulates at least part of the structure of CCR5 and interferes with the fusion of cells that express env with cells that express CD4 and CCR5. The env protein of certain HIV isolates may participate in HIV infectivity by binding to CCR5 at the surface of certain cells. While not wishing to be bound by a particular theory of the invention, the inventors believe that CCR5 variants may interfere in HIV infectivity by competing with the binding of CCR5 to env. CCR5 variants may also be useful in preventing chemokine binding, thereby ameliorating symptoms of macrophage associated immune disorders.

In one embodiment, the present invention relates to peptides and peptide derivatives that have fewer amino acid residues than CCR5 and that block membrane fusion between HIV and a target cell. Such peptides and peptide derivatives could represent research and diagnostic tools in the study of HIV infection and the development of more effective anti-HIV therapeutics. The preferred peptide fragments of CCR5 according to the invention include those which correspond to the regions of CCR5 that are exposed on the cell surface (e.g., SEQ ID NO:5, 6 or 7).

The invention relates not only to peptides and peptide derivatives of naturally-occurring CCR5, but also to CCR5 mutants and chemically synthesized derivatives of CCR5 that block membrane fusion between HIV and a target cell. For example, changes in the amino acid sequence of CCR5 are contemplated in the present invention. CCR5 can be altered by changing the DNA encoding the protein (e.g., SEQ ID NO:1 &2). Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Variants useful for the present invention comprise analogs, homologs, muteins and mimetics of CCR5 that retain. the ability to block membrane fusion. Peptides of the CCR5 refer to portions of the amino acid sequence of CCR5 that also retain this ability. The variants can be generated directly from CCR5 itself by chemical modification, by proteolytic enzyme digestion, or by combinations thereof. Additionally, genetic engineering techniques, as well as methods of synthesizing polypeptides directly from amino acid residues, can be employed.

Peptides of the intention include the following which correspond to extracelluar loops of CCR5 (amino acid designations are according to the single letter code):

```
extracellu-  (SEQ ID NO: 5)  A/LAAQWDFGNTMC
lar loop-1
(el-1):

extracellu-  (SEQ ID NO: 6)  RSQKEGLHYTCSSHFPYSQYQFWK
lar loop-2
(el-2):

extracellu-  (SEQ ID NO: 7)  QEFFGLNNCSSSNRLD
lar loop-3
(el-3):
```

FIG. 2 shows the ability of SEQ ID NO: 5, 6, and 7 to inhibit fusion between cells expressing the HIV-1 env (from the macrophage tropic Ba-L isolate) and murine cells co-expressing CD4 and CCR5.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan et al., Current Protocols in Immunology, Wiley Interscience, 1991, Unit 9). Peptides of the invention can also be synthesized by the well known solid phase peptide synthesis methods described Merrifield (J. Am. Chem. Soc., 85:2149, 1962), and Stewart and Young, Solid Phase Peptides Synthesis, (Freeman, San Francisco, 1969, pp. 27 62), using a copoly(styrene-divinylbenzene) containing 0.11.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Alternatively, peptides can be produced by recombinant methods as described below.

The term "substantially purified" as used herein refers to a molecule, such as a peptide that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify CCR5 peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Non-peptide compounds that mimic the binding and function of CCR5 ("mimetics") can be produced by the approach outlined in Saragovi et al., Science 253: 792-95 (1991). Mimetics are molecules which mimic elements of protein secondary structure. See, for example, Johnson et al.,"Peptide Turn Mimetics," in BIOTECHNOLOGY AND PHARMACY, Pezzuto et al., Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of CCR5 itself.

Longer peptides can be produced by the "native chemical" ligation technique which links together peptides (Dawson, et al., Science, 266:776, 1994). Variants can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990-93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra.

If the compounds described above are employed, the skilled artisan can routinely insure that such compounds are amenable for use with the present invention in view of the vaccinia cell fusion system described herein. If a compound blocks env-mediated membrane fusion (i) involved in HIV entry into a human CD4-positive target cell or (ii) between an HIV-infected cell and an uninfected human CD4-positive target cell, the compound is suitable according to the invention.

CCR5-Binding and Blocking Agents

In yet another embodiment, the present invention relates to CCR5-binding agents that block membrane fusion between HIV and a target cell. Such agents could represent research and diagnostic tools in the study of HIV infection and the development of more effective anti-HIV therapeutics. In addition, pharmaceutical compositions comprising CCR5-binding agents may represent effective anti-HIV therapeutics. In the context of HIV infection, the phrase "CCR5-binding agent" denotes a naturally occurring ligand of CCR5 such as, for example: RANTES, MIP-1α or MIP-1β; a synthetic ligand of CCR5, or appropriate derivatives of the natural or synthetic ligands. The determination and isolation of ligands is well described in the art. See, e.g., Lerner, *Trends NeuroSci.* 17:142-146 (1994) which is hereby incorporated in its entirety by reference. A CCR5-binding agent that blocks env-mediated membrane fusion (i) involved in HIV entry into a human CD4-positive target cell or (ii) between an HIV-infected cell and an uninfected human CD4-positive target cell is suitable according to the invention. Further, a CCR5 blocking or binding agent includes an agent which inhibits gp120 binding to CCR5 or chemokine binding to CCR5.

In yet another embodiment, the present invention relates to CCR5-binding agents that interfere with binding between CCR5 and a chemokine. Such binding agents may interfere by competitive inhibition, by non-competitive inhibition or by uncompetitive inhibition.

Interference with normal binding between CCR5 and one or more chemokines can result in a useful pharmacological effect related to inflammation because CCR5 binds chemokines that regulate monocyte accumulation and activation in inflamed tissue sites. Nevertheless, while monocyte chemotaxis is the most widely shared and perhaps best described function for MIP-1α, MIP-1β and RANTES, apparently each of the CC CKRs that bind one or more of these chemokines connect specifically and differentially to additional monocyte functions such as T-cell costimulation.

Monocytes are long-lived cells capable of further differentiation as they move from the blood to establish residence in the tissues as macrophages. The functional properties of tissue macrophages differ in different organs, and in the same organ depending on the presence of priming agents, i.e., agents that can change the behavior of monocytes and make them more sensitive to chemoattractants. CCR5-binding or blocking agents can interfere with the normal functioning of this system to reduce inflammation and are contemplated by the present invention. Anti-CCR5 antibodies of the invention are also useful in this context.

Screen for CCCKR5 Binding and Blocking Compositions

In another embodiment, the invention provides a method for identifying a composition which binds to CCR5 or blocks HIV env-mediated membrane fusion. The method includes incubating components comprising the composition and CCR5 under conditions sufficient to allow the components to interact and measuring the binding of the composition to CCR5. Compositions that bind to CCR5 include peptides, peptidomimetics, polypeptides, chemical compounds and biologic agents as described above. In addition to inhibition of cell fusion, one of skill in the art could screen for inhibition of gp120 binding or inhibition of CCR5 binding to a chemokine to determine if a compound or composition was a CCR5 binding or blocking agent.

Incubating includes conditions which allow contact between the test composition and CCR5. Contacting includes in solution and in solid phase. The test ligand(s)/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008-1012, 1985), allele-specific oligonucleotide (ASO) probe analysis (Conner, et al., *Proc. Natl. Acad Sci. USA*, 80:278, 1983), oligonucleotide ligation assays (OLAs) (Landegren, et al., *Science,* 241:1077, 1988), and the like. Molecular techniques for DNA analysis have been reviewed (Landegren, et al., *Science,* 242:229-237, 1988).

To determine if a composition can functionally complex with the receptor protein, induction of the exogenous gene is monitored by monitoring changes in the protein levels of the protein encoded for by the exogenous gene, for example. When a composition(s) is found that can induce transcription of the exogenous gene, it is concluded that this composition(s) can bind to the receptor protein coded for by the nucleic acid encoding the initial sample test composition(s).

Expression of the exogenous gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase,a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-receptor binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to CCR5. Ligands/compositions that bind to CCR5 can be assayed in standard cell:cell fusion assays, such as the vaccinia assay described herein to determine whether the composition inhibits or blocks env-mediated membrane fusion (i) involved in HIV entry into a human CD4-positive target cell or (ii) between an HIV-infected cell and an uninfected human CD4-positive target cell. Screening methods include inhibition of chemokine binding to CCR5 (e.g., use radiolabeled chemokine) or inhibition of labeled gp120. For example, a derivative of RANTES was shown to act as a CCR5 receptor antagonist (RANTES 9-68; Arenzana-Selsdedos et al., *Nature* 383:400, 1996, incorporated by reference). AOP-RANTES and Met-RANTES were shown to bind with high affinity yet failed to induce chemotaxis signalling, thereby acting as an antagonist (Simmons et al., *Science* 276:276, 1997). Thus, the screening method is also useful for identifying variants, binding or blocking agents, etc., which functionally, if not physically (e.g., sterically) act as antagonists or agonists, as desired.

Pharmaceutical Compositions

The invention also includes various pharmaceutical compositions that block membrane fusion between HIV and a target cell. The pharmaceutical compositions according to the invention are prepared by bringing an antibody against CCR5, a peptide or peptide derivative of CCR5, a CCR5 mimetic, or a CCR5-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405-1412, 1461-1487 (1975) and *The National Formulary XIV,* 14th ed. Washington: American Pharmaceutical Association (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

In another embodiment, the invention relates to a method of blocking the membrane fusion between HIV and a target cell. This method involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science,* 249: 1527-1533 (1990), which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) GOODMAN AND GILMAN'S: THE PHARMACOLOGICAL BASES OF THERAPEUTICS, 8th ed., Pergamon Press; and REMINGTON'S PHARMACEUTICAL SCIENCES, 17th ed. (1990), Mack Publishing Co., Easton, Pa., each of which is herein incorporated by reference.

Testing for New Pharmaceutical Compositions

In a preferred embodiment, the invention is a method for screening a compound ("test substance") for anti-HIV pharmacological activity. In this embodiment, the CCR5 and CD4 genes are expressed in one type of eukaryotic cell and incubated with a second type of eukaryotic cell that expresses an HIV envelope protein ("env"). Fusion between at least one cell of each type with the other type is then monitored. The test substance is added to the incubation solution before or after mixing of the cells and its effect on the fusion rate of cells is determined by any of a number of means. One means to monitor fusion is to include a system that results in the production of an active $\beta$-galactosidase upon cell fusion as described in Nussbaum et al., 1994, supra. If the test molecule inhibits HIV infectivity then the presence of the molecule will decrease the cell fusion response. In the case where the test substance binds a naturally occurring molecule present in the human that is necessary for HIV infectivity, then addition of the test molecule may decrease cell fusion.

The cell fusion assay can be used to determine the functional ability of CCR5 to confer env-mediated fusion competence to a diverse range of CD4-positive (e.g., either recombinantly produced or naturally occurring) cell types: e.g., NIH 3T3 (murine); BS-C-1 (African green monkey); HEK293 (human); and Mv 1 Lu (mink). In addition, unusual, fusion-incompeterit, CD4-positive human cell types can be employed (U-87 MG glioblastoma; and SCL1).

Variations of drug screening methods are known to the artisan of average skill in this field. Consequently, the cell fusion assay can be used in a wide variety of formats to exploit the properties of the CCR5 receptor to screen for drugs that are effective against HIV.

Antisense or Ribozyme Inhibition of CCR5 for HIV Therapy

Antisense technology offers a very specific and potent means of inhibiting HIV infection of cells that contain CCR5, for example, by decreasing the amount of CCR5 expression in a cell. Antisense polynucleotides in context of the present invention includes both short sequences of DNA known as oligonucleotides of usually 10-50 bases in length as well as longer sequences of DNA that may exceed the length of the CCR5 gene sequence itself. Antisense polynucleotides useful for the present invention are complementary to specific regions of a corresponding target mRNA. Hybridization of antisense polynucleotides to their target transcripts can be highly specific as a result of complementary base pairing. The capability of antisense polynucleotides to hybridize is affected by such parameters as length, chemical modification and secondary structure of the transcript which can influence polynucleotide access to the target site. See Stein et al, *Cancer Research* 48:2659 (1988). An antisense polynucleotide can be introduced to a cell by introducing a DNA segment that codes for the polynucleotide into the cell such that the polynucleotide is made inside the cell. An antisense polynucleotide can also be introduced to a cell by adding the polynucleotide to the environment of the cell such that the cell can take up the polynucleotide directly. The latter route is preferred for the shorter polynucleotides of up to about 20 bases in length.

In selecting the preferred length for a given polynucleotide, a balance must be struck to gain the most favorable characteristics. Shorter polynucleotides such as 10-to 15-mers, while offering higher cell penetration, have lower gene specificity. In contrast, while longer polynucleotides of 20-30 bases offer better specificity, they show decreased uptake kinetics into cells. See Stein et al., PHOSPHOROTHIOATE OLIGODEOXYNUCLEOTIDE ANALOGUES in "Oligodeoxynucleotides—Antisense Inhibitors of Gene Expression" Cohen. ed. McMillan Press, London (1988). Accessibility to mRNA target sequences also is of importance and, therefore, loop-forming regions in targeted mRNAs offer promising targets.

In this disclosure the term "polynucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such polynucleotides may be prepared by methods well-known in the art, for instance using commercially available machines and reagents available from Perkin-Elmer/Applied Biosystems (Foster City, Calif.).

Phosphodiester-linked polynucleotides are particularly susceptible to the action of nucleases in serum or inside cells, and therefore in a preferred embodiment the polynucleotides of the present invention are phosphorothioate or methyl phosphonate-linked analogues, which have been shown to be nuclease-resistant. Persons of ordinary skill in this art will be able to select other linkages for use in the invention. These modifications also may be designed to improve the cellular uptake and stability of the polynucleotides.

In another embodiment of the invention, the antisense polynucleotide is an RNA molecule produced by introducing an expression construct into the target cell. The RNA molecule thus produced is chosen to have the capability to hybridize to CCR5 mRNA. Such molecules that have this capability can inhibit translation of the CCR5 mRNA and thereby inhibit the ability of HIV to infect cells that contain the RNA molecule.

The polynucleotides which have the capability to hybridize with mRNA targets can inhibit expression of corresponding gene products by multiple mechanisms. In "translation arrest," the interaction of polynucleotides with target mRNA blocks the action of the ribosomal complex and, hence, prevents translation of the messenger RNA into protein. Haeuptle et al., *Nucl. Acids. Res.* 14:1427 (1986). In the case of phosphodiester or phosphorothioate DNA polynucleotides, intracellular RNase H can digest the targeted RNA sequence once it has hybridized to the DNA oligomer. Walder and Walder, *Proc. Natl. Acad Sci. USA* 85:5011 (1988). As a further mechanism of action, in "transcription arrest" it appears that some polynucleotides can form "triplex," or triple-helical structures with double stranded genomic DNA containing the gene of interest, thus interfering with transcription by RNA polymerase. Giovannangeli et al., *Proc. Natl. Acad. Sci.* 90:10013 (1993); Ebbinghaus et al. *J. Clin. Invest.* 92:2433 (1993).

In one preferred embodiment, CCR5 polynucleotides are synthesized according to standard methodology. Phosphorothioate modified DNA polynucleotides typically are synthesized on automated DNA synthesizers available from a variety of manufacturers. These instruments are capable of synthesizing nanomole amounts of polynucleotides as long as 100 nucleotides. Shorter polynucleotides synthesized by modern instruments are often suitable for use without further purification. If necessary, polynucleotides may be purified by polyacrylamide gel electrophoresis or reverse phase chromatography. See Sambrook et al., *MOLECULAR CLONING: A Laboratory Manual*, Vol. 2, Chapter 11, Cold Spring Harbor Laboratory Press, Cold Spring Harbor, N.Y. (1989).

Alternatively, a CCR5 polynucleotide in the form of antisense RNA may be introduced to a cell by its expression within the cell from a standard DNA expression vector. CCR5 DNA antisense sequences can be cloned from standard plasmids into expression vectors, which expression vectors have characteristics permitting higher levels of, or more efficient expression of the resident polynucleotides. At a minimum, these constructs require a prokaryotic or eukaryotic promoter sequence which initiates transcription of the inserted DNA sequences. A preferred expression vector is one where the expression is inducible to high levels. This is accomplished by the addition of a regulatory region which provides increased transcription of downstream sequences in the appropriate host cell. See Sambrook et al., Vol. 3, Chapter 16 (1989).

For example, CCR5 antisense expression vectors can be constructed using the polymerase chain reaction (PCR) to amplify appropriate fragments from single-stranded cDNA of a plasmid such as pRc in which CCR5 cDNA has been incorporated. Fang et al., *J. Biol Chem.* 267:25889 25897 (1992). Polynucleotide synthesis and purification techniques are described in Sambrook et al. and Ausubel et al. (eds), CURRENT PROTOCOlS IN MOLECULAR BIOIOLOGY (Wiley Interscience 1987) (hereafter "Ausubel"), respectively. The PCR procedure is performed via well-known methodology See, for example, Ausubel, and Bangham, "The Polymerase Chain Reaction: Getting Started," in PROTOCOLS IN HUMAN MOLECULAR GENETICS (Humana Press 1991). Moreover, PCR kits can be purchased from companies such as Stratagene Cloning Systems (La Jolla, Calif.) and invitrogen (San Diego, Calif. ).

The products of PCR are subcloned into cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Suitable cloning vectors are described by Sambrook et al., Ausubel, and Brown (ed.), MOLECULAR BIOLOGY LABFAX (Academic Press 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

Preferably, the PCR products are ligated into a "TA" cloning vector. Methods for generating PCR products with a thymidine or adenine overhang are well-known to those of skill in the art. See, for example, Ausubel at pages 15.7.1-15.7.6. Moreover, kits for performing TA cloning can be purchased from companies such as Invitrogen (San Diego, Calif.).

Cloned antisense fragments are amplified by transforming competent bacterial cells with a cloning vector and growing the bacterial host cells in the presence of the appropriate antibiotic. See, for example, Sambrook et al., and Ausubel. PCR is then used to screen bacterial host cells for CCR5 antisense orientation clones. The use of PCR for bacterial host cells is described, for example, by Hofmann et al., "Sequencing DNA Amplified Directly from a Bacterial Colony," in PCR PROTOCOLS: METHODS AND APPLICATIONS, White (ed.), pages 205-210 (Humana Press 1993), and by Cooper et al., "PCR-Based Full-Length cDNA Cloning Utilizing the Universal-Adaptor/Specific DOS Primer-Pair Strategy," Id. at pages 305-316.

Cloned antisense fragments are cleaved from the cloning vector and inserted into an expression vector. For example, HindIII and XbaI can be used to cleave the antisense fragment from TA cloning vector pCR™-II (Invitrogen;San Diego, Calif.). Suitable expression vectors typically contain (1) prokaryotic DNA elements coding for a bacterial origin of replication and an antibiotic resistance marker to provide for the amplification and selection of the expression vector in a bacterial host; (2) DNA elements that control initiation of transcription, such as a promoter; and (3) DNA elements that control the processing of transcripts, such as a transcription termination/polyadenylation sequence.

For a mammalian host, the transcriptional and translational regulatory signals preferably are derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1: 273 (1982)); the TK promoter of Herpes virus (McKnight, *Cell* 31: 355 (1982)); the SV40 early promoter (Benoist et al, *Nature* 290: 304 (1981)); the Rous sarcoma virus promoter (Gorman et al., *Proc. Nat'l Acad. Sci. USA* 79: 6777 (1982)); and the cytomegalovirus promoter (Foecking et al., *Gene* 45: 101 (1980)).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10: 4529 (1990); Kaufman et al., *Nucl. Acids Res.* 19: 4485 (1991).

A vector for introducing at least one antisense polynucleotide into a cell by expression from a DNA is the vector pRc/CMV (Invitrogen, San Diego, Calif.), which provides a high level of constitutive transcription from mammalian enhancer-promoter sequences. Cloned CCR5 antisense vectors are amplified in bacterial host cells, isolated from the cells, and analyzed as described above.

Another possible method by which antisense sequences may be exploited is via gene therapy. Virus-like vectors, usually derived from retroviruses, may prove useful as vehicles for the importation and expression of antisense constructs in human cells. Generally, such vectors are non-replicative in vivo, precluding any unintended infection of non-target cells. In such cases, helper cell lines are provided which supply the missing replicative functions in vitro, thereby permitting amplification and packaging of the antisense vector. A further precaution against accidental infection of non-target cells involves the use of target cell-specific regulatory sequences. When under the control of such sequences, antisense constructs would not be expressed in normal tissues.

Two prior studies have explored the feasibility of using antisense polynucleotides to inhibit the expression of a heparin binding growth factor. Kouhara et al., *Oncogene* 9: 455-462 (1994); Morrison, *J. Biol. Chem.* 266: 728 (1991). Kouhara et al showed that androgen-dependent growth of mouse mammary carcinoma cells (SC-3) is mediated through induction of androgen-induced, heparin binding growth factor (AIGF). An antisense 15-mer corresponding to the translation initiation site of AIGF was measured for its ability to interfere with androgen-induction of SC-3 cells. At -concentrations of 5 µM, the antisense polynucleotide effectively inhibited androgen-induced DNA synthesis. Morrison showed that antisense polynucleotides targeted against basic fibroblast growth factor can inhibit growth of astrocytes in culture. Thus, the general feasibility of targeting an individual gene product in a mammalian cell has been established.

Antisense polynucleotides according to the present invention are derived from any portion of the open reading frame of the CCR5 cDNA. Preferably, mRNA sequences (i) surrounding the translation initiation site and (ii) forming loop structures are targeted. Based upon the size of the human genome, statistical studies show that a DNA segment approximately 14-15 base pairs long will have a unique sequence in the genome. To ensure specificity of targeting CCR5 RNA, therefore, it is preferred that the antisense polynucleotides are at least 15 nucleotides in length. Thus, the shortest polynucleotides contemplated by the present invention encompass nucleotides corresponding to positions 1-14, 1-15, 1-16, 1-17, 1-18, 1-19, 2-16, 3-17, etc. of the CCR5 cDNA sequence. Position 1 refers to the first nucleotide of the CCR5 coding region.

Not every antisense polynucleotide will provide a sufficient degree of inhibition or a sufficient level of specificity for the CCR5 target. Thus, it will be necessary to screen polynucleotides to determine which have the proper antisense characteristics. A preferred method to assay for a useful antisense polynucleotide is the inhibition of cell fusion between: (1) cells that contain CD4 and CCR5; and (2) cells that contain env.

Administration of an antisense polynucleotide to a subject, either as a naked, synthetic polynucleotide or as part of an expression vector, can be effected via any common route (oral, nasal, buccal, rectal, vaginal, or topical), or by subcutaneous, intramuscular, intraperitoneal, or intravenous injection. Pharmaceutical compositions of the present invention, however, are advantageously administered in the form of injectable compositions. A typical composition. for such purpose comprises a pharmaceutically acceptable solvent or diluent and other suitable, physiologic compounds. For instance, the composition may contain polynucleotide and about 10 mg of human serum albumin per milliliter of a phosphate buffer containing NaCl.

As much as 700 milligrams of antisense polynucleotide has been administered intravenously to a patient over a course of 10 days (i.e., 0.05 mg/kg/hour) without signs of toxicity. Sterling,. "Systemic Antisense Treatment Reported," *Genetic Engineering News* 12: 1, 28 (1992).

Other pharmaceutically acceptable excipients include non-aqueous aqueous solutions and non-toxic compositions including salts, preservations, buffers and the like. Examples of non aqueous solutions are propylene glycol, polyethylene glycol, vegetable oil and injectable organic esters such as ethyloleate. Aqueous solutions include water, alcoholic/ aqueous solutions, saline solutions, parenteral vehicles such as sodium chloride, Ringe's dextrose, etc. Intravenous vehicles include fluid and nutrient replenishers. Preservatives include antimicrobial, anti-oxidants, chelating agents and inert gases. The pH and exact concentration of the various components of the pharmaceutical composition are adjusted according to routine skills in the art. A preferred pharmaceutical composition for topical administration is a dermal cream or transdermal patch.

Antisense polynucleotides or their expression vectors may be administered by injection as an oily suspension. Suitable lipophilic solvents or vehicles include fatty oils, such as sesame oil, or synthetic fatty acid esters, such as ethyl oleate or triglycerides. Moreover, antisense polynucleotides or vectors may be combined with a lipophilic carrier such as any one of a number of sterols including cholesterol, cholate and deoxycholic acid. A preferred sterol is cholesterol. Aqueous injection suspensions may contain substances which increase the viscosity of the suspension, for example, sodium carboxymethyl cellulose, sorbitol, and/or dextran. Optionally, the suspension also contains stabilizers.

An alternative formulation for the administration of antisense CCR5 polynucleotides involves liposomes. Liposome encapsulation provides an alternative formulation for the administration of antisense CCR5 polynucleotides and expression vectors. Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46: 618 (1993). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s). See, for example, Machy et al., LIPOSOMES IN CELL BIOLOGY AND PHARMACOLOGY (John Libbey 1987), and Ostro et al., *American J. Hosp. Pharm.* 46: 1576 (1989). Moreover, lit is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N.Y. Acad Sci.* 446: 368 (1985).

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biophys. Acta* 1150: 9 (1993). These Stealth® liposomes have an increased circulation time and an improved targeting to tumors in animals. Woodle et al., *Proc. Amer. Assoc. Cancer Res.* 33: 2672 (1992). Human clinical trials are in progress, including Phase III clinical trials against Kaposi's sarcoma. Gregoriadis et al., *Drugs* 45: 15 (1993).

Antisense polynucleotides and expression vectors can be encapsulated within liposomes using standard techniques. A variety of different liposome compositions and methods for synthesis are known to those of skill in the art. See, for example, U.S. Pat. No. 4,844,904, U.S. Pat. No. 5,000,959, U.S. Pat. No. 4,863,740, and U.S. Pat. No. 4,975,282, all of which are hereby incorporated by reference.

Liposomes can be prepared for targeting to particular cells or organs by varying phospholipid composition or by inserting receptors or ligands into the liposomes. For instance, antibodies specific to tumor associated antigens may be incorporated into liposomes, together with antisense polynucleotides or expression vectors, to target the liposome more effectively to the tumor cells. See, for example, Zelphati el al., *Antisense Research and Development* 3: 323-338 (1993), describing the use "immunoliposomes" containing antisense polynucleotides for human therapy.

In general, the dosage of administered liposome-encapsulated antisense polynucleotides and vectors will vary depending upon such factors as the patient's age, weight, height, sex, general medical condition and previous medical history. Dose ranges for particular formulations can be determined by using a suitable animal model.

The above approaches can also be used not only with antisense nucleic acid, but also with ribozymes, or triplex agents to block transcription or translation of a specific CCR5 mRNA, either by masking that MRNA with an antisense nucleic acid or triplex agent, or by cleaving it with a ribozyme.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1(3):227, 1991; Helene, C., *Anticancer Drug Design,* 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Homozygous and Heterozygous Mutations in CCR5

It is known that in some cases, a homozygous or heterozygous mutation in a polypeptide or a regulatory region of a gene confers a molecular basis for a difference in function. Bertina, et al. and Greengard, et al. (Bertina, et al., *Nature,* 369:64, 1994; Greengard, et al., *Lancet,* 343:1361, 1994), first identified the molecular basis for the FV abnormality. The phenotype of APC resistance was shown to be associated with heterozygosity or homoygosity for a single point mutation in the FV gene that resulted in the substitution of arginine at amino acid residue 506 with glutamine (FV R506Q). This R506Q mutation prevents APC from cleaving a peptide bond at Arg-506 in FV that is required to inactivate factor Va (Bertina, supra; Sun, et al., *Blood*, 83:3120, 1994).

Similarly, the present invention envisions diagnostic and prognostic, and in addition, therapeutic approaches to treatment of HIV-associated syndromes based on homozygosity or heterozygosity of CCR5 mutants. For example, while not wanting to be bound by a particular theory, it is believed that a subject having a homozygous mutant of CCR5 may be HIV resistant or exhibit a slower rate of disease progression. Along the same lines, a subject having a heterozygous mutation in CCR5 may exhibit a slower rate of disease progression than a patient having a wild type CCR5. Mutations included in the CCR5 coding region may also result in inactivating mutations. In addition, a mutation in the regulatory region of CCR5 gene may prevent or inhibit expression of CCR5, thereby providing resistance to some degree from HIV infection.

Once an individual having a homozygous or heterozygous mutant in CCR5 is identified, it is envisioned that cells from that individual, once matched for histocormpatibility, can be transplanted to an HIV positive individual, or to an "at risk" individual.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Cloning and Sequence Analysis of the CCR5 Gene

Complementary DNAs were obtained from a λgt11 cDNA library (Combadiere et al., *DNA Cell Biol.* cit op.). One of the cDNAs obtained, designated clone 63-2, had a novel sequence highly related to CC CKR2B, but it extended only from-bp 105 to 813 of the CC CKR2B open reading frame. The 63-2 cDNA was used as a hybridization probe to screen under low stringency conditions (final wash in 5× SSPE: described by Maniatis et al., Molecular Cloning a Laboratory Manual, Cold Spring Harbor Laboratory, at 55° C. for 30 min) a λpCEV9 cDNA library prepared from endotoxin-stimulated human peripheral blood monocytes as described previously (Combadiere et al., *J. Biol. Chem.* 270: 29671-5 and *J. Biol. Chem.* 270: 16491-4 (1995)). One of the isolated clones, designated clone 8.5, matched 15 and extended the sequence of clone 63-2. A 1.4 kb fragment of the clone 8.5 cDNA was excised from the vector DNA by Bam HI and Bst XI double digestion, blunt-ended with Pfu DNA polymerase, subcloned into the Eco RV site of pBluescript II KS (Stratagene, La Jolla, Calif.), and sequenced completely on both strands. The cDNA insert was then subcloned between the Bam HI and Hind III sites of the mammalian expression vector pREP9 (Invitrogen, San Diego, Calif.).

The clone 8.5 cDNA is 1.4 kb in length. The 5'- and 3'-untranslated regions and open reading frame are 26,288 and 1056 bp, respectively. The 3'-untranslated region is not polyadenylated and lacks a polyadenylation consensus sequence. The ATG codon proposed to initiate translation is flanked by sequence that conforms favorably with established consensus rules. M. Kozak, *Nucleic Acids Res.* 15: 8125-48 (1987). The open reading frame contains 352 codons.

Seven segments of the deduced amino acid sequence from SEQ ID NO: 1 have a high content of hydrophobic amino acids consistent with membrane-spanning domains as well as multiple amino acids conserved in analogous positions of the known seven-transmembrane-domain receptor rhodopsin. These considerations clearly indicate that CCR5 is ancestrally related to rhodopsin-like receptors, and strongly suggest that it functions as a seven-transmembrane-domain G protein-coupled receptor. A database search revealed that the highest sequence identity occurs with chemokine receptors. In particular, the amino acid sequence of CCR5 is 57, 70, 75, 51 and 48% identical to CC CKR1, CC CKR2A, CC CKR2B, CC CKR3 and CC CKR4, respectively, with lower identity (approximately 30%) to the CXC chemokine receptors, IL-8 receptors A and B. An alignment of the amino acid sequence of CCR5 ["SEQ ID NO: 2"] with those of CC CKR1 and CC CKR2B is shown in FIG. 1.

The CC CKR2B sequence is eight amino acids longer than CCR5 due to a substantially longer N-terminal segment. The two sequences are otherwise colinear with the exception of a four amino acid gap in the putative second extracellular loop of CC CKR2B relative to that of CCR5.

Residues of CCR5 that differ from CC CKR2B in the alignment are found mostly in the putative extracellular domains (the N terminal segment and the sequence between putative transmembrane domains 2 and 3, 4 and 5, and 6 and 7) and adjacent portions of the transmembrane domains, and in the C-terminal segment which is predicted to lie in the cytoplasm (FIG. 2). Like other seven-transmembrane-domain receptors, the C-terminal tail has a high content of serine and threonine residues that may be sites for receptor phosphorylation as they are in rhodopsin and the β2 adrenergic receptor. CCR5 also contains cysteine residues that by analogy with other seven-transmembrane domain receptors could be a site for palmitoylation, tethering this domain to the plasma membrane.

The net charge of the N-terminal extracellular segment of CCR5 is −1. The corresponding domain of CC CKR2B has a net charge of zero, whereas for other known chemokine receptors this domain is highly acidic. Like all other known chemokine receptors, CCR5 has conserved cysteine residues in the N-terminal segment and the third predicted extracellular loop that could form a disulfide bond. Cysteine residues are less frequently found in this location in other seven-transmembrane-domain receptors. CCR5 lacks a consensus sequence for N-linked glycosylation, whereas one or more are found in other CC CKR's.

The CCR5 Gene. When total human genomic DNA was digested with Pst I, Eco RI, Hind III and Xba I and hybridized with a CCR5 cDNA probe extending from bp 69 to 789 relative to the start of the open reading frame, 2 4 bands that hybridized with different intensity were detected in each lane. The probe used contains a recognition site for Pst I at bp 532 of the CCR5 open reading frame but not for the other restriction enzymes used. The pattern is most consistent with multiple small cross-hybridizing genes. In fact, restriction fragments of genomic clones isolated for CC CKR2, CC CKR3 and CCR5 can account for all of the bands seen. The CC CKR2B, CC CKR3 and CCR5 open reading frames lack intervening sequences.

EXAMPLE 2

Chemokine Binding to CCR5

Human embryonic kidney (HEK) 293 cells (a total of $10^7$) grown to log phase in DMEM and 10% fetal bovine serum were electroporated with 20 µg of plasmid DNA, and G418-resistant colonies were picked and expanded as described previously (Combadiere et al., op cit.). The cell lines studied contained large amounts of the recombinant CCR5 mRNA, but lacked CC CKR3 mRNA and native 8.5 mRNA, as assessed by Northern blot analysis of total RNA using full-length cDNA probes. The methods used to create HEK 293 cell lines stably expressing CC CKR1 and CC CKR2B have been described previously (Combadiere et al., J. Biol. Chem. 270: 29671-5).

Transfected HEK 293 cells (a total of $10^6$) were incubated in duplicate with 0.2 nM $^{125}$I-labeled RANTES, MCP-1, MIP-1α, MIP-1β or MCP-3 (specific activity ~2200 Ci/mmol, Du Pont/NEN, Boston, Mass.) and varying concentrations of unlabeled recombinant human chemokines (Peprotech, Rocky Hill, N.J.) in 200 µl of binding medium (RPMI 1640 with 1 mg/ml BSA and 25 mM HEPES, pH 7.4). After incubation for 1 h at 4° C. or 37° C., unbound chemokines were separated from cells by pelleting through a 10% sucrose/PBS cushion, and the cell-associated counts were determined. Specific binding was determined by the difference in counts in the presence and absence of 1250-fold molar excess of unlabeled chemokine.

Receptor activation from chemokine binding was assessed by real time measurement of $[Ca^{2+}]_i$ changes using 2 million transfected HEK 293 cells loaded with FURA-2. Ratio fluorescence of cells was measured as described previously. Combadiere et al., J. Biol. Chem. 270: 16491-4 (1995). J. Van Damme (Rega Institute, Leuven) provided chemically synthesized human MCP-2 protein according to a procedure described in Proost et al., Cytokine 7: 97-104 (1995). O. Yoshie (Shionogi Institute, Osaka) provided recombinant human eotaxin. Where indicated, cells loaded with FURA-2 were incubated in holotoxin of B. pertussis (List, Campbell, Calif.) 250 ng/ml for 2 h at 37° C., then washed twice in PBS and resuspended in HBSS. Cell viability was ~80% by trypan blue exclusion after pertussis toxin treatment. ATP was purchased from Sigma Co. (St. Louis, Mo.).

Agonists for CCR5. Given the high sequence similarity of CCR5 with other CC chemokine receptors, the inventors predicted that CCR5 would be specific for CC chemokines. To test this, the inventors transfected HEK 293 cells, which normally are unresponsive to stimulation with chemokines, with the clone 8.5 cDNA and measured the calcium flux responses induced by a panel of chemokines. The calcium flux response is strongly associated with chemotaxis, degranulation and other higher order leukocyte responses to chemokines, and is a sensitive and specific measure of receptor activation. Neither untransfected nor mock-transfected and selected HEK 293 cells responded to any of the chemokines tested. In contrast, six independent HEK 293 cell lines stably transfected with the clone 8.5 CDNA, three each from two separate transfections, exhibited $[Ca^{2+}]_i$ transients in response to MIP-1α, RANTES and MIP-1β, but not in response to MCP-1, MCP-2, MCP-3, eotaxin, IL-8 or γIP-10 all tested at 100 nM. MIP-1α, MIP-1β and RANTES were similar in potency and efficacy, the concentrations for half-maximal and maximal responses ranging from 540 and 25-50 nM, respectively. These results indicate that CCR5 is a CC chemokine receptor selective for MIP-1α, MIP-1β and RANTES.

Desensitization of CCR5. After activation, chemokine receptors have altered sensitivity to repeated stimulation with the activating agonist and other agonists. When the same chemokine, was added in succession to CCR5 transfectants, cells responded to the first addition but not the second, indicating that the receptor underwent homologous desensitization to all three of its agonists. When different agonists were added in succession, MIP-1α or RANTES given first blocked the response to MIP-1β given second, and MIP-1β or RANTES given first blocked the response to MIP-1α given second. But MIP-1α or MIP-1β given first reduced, but did not eliminate, the response to RANTES given second. MCP-1 had no effect on the responses to MIP-1α, MIP-1β or RANTES. These data show a functional interaction of MIP-1α, MIP-1β and RANTES with the same receptor, CCR5.

G Protein Coupling to CCR5. Known chemokine receptors couple to $G_i$-type C proteins, which unlike other classes of G proteins are functionally sensitive to pertussis toxin. Treatment of CCR5 transfectants with pertussis toxin completely abolished the calcium flux response to MIP-1α, MIP-1β and RANTES. In contrast, the calcium flux response to ATP was largely unaffected. These data indicate that CCR5 in HEK 293 cells is coupled to G proteins of the $G_i$ class.

Binding of CC Chemokines to CCR5. The calcium flux results show that cells expressing CCR5 have acquired the capacity to respond to the presence of MIP-1α, MIP-1β and RANTES. The mechanism of this effect appears to be related to specific binding to CCR5 on the cell surfaces as judged by radioligand binding assays with intact HEK 293 cells that were stably transfected with CCR5 and by comparison with HEK 293 cells stably transfected with CC CKR1 and CC CKR2B as positive and negative controls, respectively. The results for CCR5 are quite complex, and the results for the positive and negative controls are described first.

The total amounts of $^{125}$I-MIP-1α, $^{125}$I-MIP-1β and $^{125}$I-RANTES that bound to CC CKR2B were similar in magnitude to untransfected HEK 293 cells, and were completely non-specific in both cases, whether the assays were carried out at 4° C. or 37° C. In contrast, CC CKR2B transfectants specifically bound both $^{125}$I-MCP-1 and $^{125}$I-MCP-3 at both 4° C. and 37° C. These results are consistent with the known agonists for CC CKR2B.

In the case of CC CKR1, specific binding of $^{125}$I-MIP-1α was 5-10-fold greater than non-specific binding at both 4° C. and 37° C., whereas specific binding of $^{125}$I-MCP-1 was not detectable. The $K_i$ for homologous competition binding of $^{125}$I-MIP-1α at 4° C. was 10 nM. These results are similar to previously published results, are consistent with MIP-1α's agonist activity for CC CKR1, and represent a positive control for MIP-1α binding. Each of the six CCR5 transfectants were tested at 4° C. The total binding of $^{125}$I-MIP-1α, $^{125}$I-MIP-1β and $^{125}$I-RANTES was equal to the background levels established for the CC CKR2B transfectant, and was completely non-specific even when radioligand concentrations as high as 5 nM were tested. Yet, all six cell lines exhibited clear and robust calcium flux responses to MIP-1α, MIP-1β and RANTES.

The G418 concentration in the media of the CCR5 transfectant that exhibited the strongest calcium flux response was increased from 1 to 3 mg/ml for one week. A cell line was derived, named CCR5.1 that exhibited calcium flux responses to MIP-1α, MIP-1β and RANTES that were consistently double those of the parental cell line. This cell line exhibited specific binding at 4° C. for MIP-1α, MIP-1β and RANTES.

To increase the sensitivity of the binding assay, non-equilibrium conditions at 37° C. were used to increase the ratio of specific to non-specific binding for $^{125}$I-MIP1α, $^{125}$I-MIP-1β, and $^{125}$I-RANTES by a factor of 24 for both CC CKR1 and CCR5.1 cell lines, compared to results obtained at 4° C. $^{125}$I-MCP-1 did not bind specifically to either CC CKR1 or CCR5.1 cells at 37° C., whereas $^{125}$I-MCP-3 bound specifically to CC CKR1 but not to CCR5.1 cells.

The $^{125}$I-MIP-1α and $^{125}$I-MIP-1β binding sites on CC CKR1 and CCR5.1 cells were easily distinguished in two ways. First, $^{125}$I-MIP-1α and $^{125}$I-MIP-1βbinding to CC CKR1, but not to CCR5.1, was competed effectively by unlabeled MCP-3. Second, unlabeled MIP-1α competed 20-fold more effectively for $^{125}$I-MIP-1α binding to CC CKR1 than to CCR5.1 (half-maximal inhibitory concentrations [$IC_{50}$]~5 and 100 nM, respectively), and unlabeled MIP-1β competed-2-fold more effectively for $^{125}$I-MIP-1β binding to CCR5.1 than to CC CKR1 $IC_{50}$s~100 and 200 nM, respectively).

At 37° C., $^{125}$I-RANTES bound to both CC CKR1 and CCR5.1 cells at low but significantly increased levels compared to the negative control CC CKR2B cells. Excess unlabeled RANTES reduced $^{125}$I-RANTES binding to CCR5.1 cells ($IC_{50}$~80 nM). The $^{125}$I-RANTES binding sites on CC CKR1 and CCR5.1 could be distinguished by heterologous competition with excess unlabeled MIP-1..alpha. ($IC_{50}$-20 and 100 nM for CC CKR1 and CCR5.1 respectively).

Distribution of CCR5 RNA. Compared to other CC CKRs, CCR5 is most like CC CKR2A and CC CKR2B not only in its primary sequence but also in its RNA distribution. Full-length CC CKR2B and CCR5 open reading frame probes recognized a 3.5 kb RNA band by Northern blot hybridization in total RNA made from adherent monocytes. Neither probe recognized RNA in neutrophil or eosinophil samples. To determine whether the CCR5 probe was merely cross-hybridizing to the monocyte CC CKR2 mRNA, a 30-mer antisense oligonucleotide specific for CCR5 was designed. This probe also detected the 3.5 kb monocyte mRNA species. A similar analysis using specific oligonucleotide probes has indicated that both CC CKR2A and CC CKR2B RNA is present in adherent monocytes.

EXAMPLE 3

Cell Fusion Assay Suitable for Drug Screening

A vaccinia cell fusion system is used to assay the functional ability of CCR5 to confer env-mediated fusion competence to CD4-positive nonhuman cells. This assay is carried out as described in Nussbaum et al., 1994, supra. In the assay murine NIH 3T3 cells or human HeLa cells are first transfected with the plasmid pSC59.CCR5 and then co-infected with various vaccinia viruses: vTF7-3 (containing the T7 RNA polymnerase gene); vCB3 (containing the human CD4 gene); and vaccinia WR (a negative control). A different cell population is co-infected with various vaccinia viruses: vCB-21R (containing the E. coli lacZ gene under the transcriptional control of a T7 promoter ($P_{T7}$-lacZ)) along with either a vaccinia virus that encodes a Ba-L env gene from a macrophage-tropic isolate or vCB-16 (a negative control, containing a mutant env gene encoding an uncleavable, nonfusogenic unc/env).

The cell populations described above are incubated overnight at 31° C. to allow expression of the vaccinia-encoded proteins. The cells are washed and mixtures of each combination are prepared in 96-well microtiter plates. Each well contains equal numbers of T7 RNA polymerase-containing cells and lacZ gene-containing cells. Replicate plates are incubated for 2-4 hours at 37° C. to allow fusion. Samples on one plate are treated with NP-40 and aliquots are assayed for β-galactosidase activity using a 96-well absorbance reader.

The β-galactosidase assay results from this experiment will show that NIH 3T3 cells coexpressing human CD4 and CCR5 are highly competent for fusion with cells expressing env from the macrophage-tropic isolate (Ba-L) but not from a T-cell line-tropic isolate (LAV). In contrast, the data will indicate that NIH 3T3 cells coexpressing human CD4 alone or CCR5 alone are incompetent for fusion with cells expressing env. Furthermore, the low background levels of β-galactosidase produced will indicate that NIH 3T3 cells coexpressing human CD4 and CCR5 do not fuse with cells expressing mutant unc/env.

In a related experiment, several colonies of stable, transformed mink cells that coexpress human CD4 and CCR5 would be tested for susceptibility to HIV-1 infection by macrophage-tropic or dual-tropic HIV-1 strains (e.g., strains that use CCR5). Transformants containing the human CD4 gene and an irrelevant control gene are used as negative controls. Direct measurements of p24 (HIV core antigen) production will indicate that HIV-1 infection is productive with cells that coexpress human CD4 and CCR5, but not with the negative controls. Moreover, the efficiency of HIV-1 infection of transformed, CD4-positive, CCR5-positive, nonhuman cells is high enough to be detected directly.

EXAMPLE 4

Anti-CCR5 Antibody Blocks env-mediated Membrane Fusion

Based on the known topology of 7-transmembrane segment proteins, four regions of CCR5 are predicted to be exposed at the cell surface. Natural or synthetic peptides are produced or synthesized by methods well-known in the art that correspond to each of these 4 regions. Rabbit antisera is raised by immunization with peptide-KLH (keyhole limpet hemocyanin) conjugates. Total immunoglobulin is purified from the preimmune and the immune sera by chromatographic separation with Protein-A Sepharose. Alternatively, whole cells expressing CCR5 can be used to generate anti-CCR5 antibodies.

Antibodies raised against an 28 amino acid N-terminal portion of CCR5 or against the extracellular loops (e.g., el-1), can block membrane fusion between macrophage-tropic strains Ba-L, SF162, JR-FL and ADA of HIV and human macrophages, in other words strains that use CCR5. (See, for example, Feng et al., 1996, supra; Endres et al., 1996, supra).

EXAMPLE 5

Specificity of CCR5 for env from Macrophage-tropic Isolates

The sensitivity of fusion mediated by env from different HIV isolates is tested with antibodies prepared against the N-terminal portion of CCR5. The anti-CCR5 antibodies inhibit fusion mediated by the prototypic macrophage-tropic Ba-L env, but will not inhibit fusion mediated by the prototypic T-cell line-tropic LAV env. The fusion inhibition with anti-CCR5 antibodies is not due to nonspecific inhibitory effects on the cells. Coexpression of CCR5 enhances fusion more with env from macrophage-tropic strains (Ba-L, SF162, JR-FL, and ADA) than with env from T-cell line-tropic isolates (IIIB, LAV, and RF).

EXAMPLE 6

CCR5 Peptides Block env-mediated Membrane Fusion

Synthetic peptides that correspond to the predicted extracellular loops of CCR5 were prepared and tested for inhibition of env-mediated membrane fusion. Peptides were as follows:

```
extracellu-   (SEQ ID NO: 5) LAAQWDFGNTMC
lar loop-1:

extracellu-   (SEQ ID NO: 6) RSQKEGLHYTCSSHFPYSQYQFWK
lar loop-2:

extracellu-   (SEQ ID NO: 7) QEFFGLNNCSSSNRLD
lar loop-3:
```

The peptides were tested using vaccinia-based expression and reporter gene assay system (see Example 3 above). Cell fusion was quantitated by determining the level of β-galactosidase in detergent cell lysates.

FIG. 2 shows that each peptide (0-50 µg/ml) was able to inhibit fusion between cells expressing the HIV-1 Env from the macrophage-tropic Ba-L isolate and murine cells co-expressing CD4 and CCR5.

EXAMPLE 7

Cell Lines Expressing CCR5

Human HeLa, human embryonic kidney (HEK) 293, and murine NIH 3T3 cell lines (American Type Culture Collection, Rockville, Md.) were cultured in DMEM-10 (Dulbecco's modified Eagle's medium [Quality Biologicals, Gaithersburg, Md.] containing 10% fetal bovine serum [FBS, HyClone, Logan, Utah], 2 mM L-glutamine, 100 U/ml penicillin and 100 µg/ml streptomycin). The human PM1 T cell line (Lusso et al., 1995) was obtained from the NIH AIDS Research and Reference Reagent Program (Rockville, Md.) and was grown in RPMI-10 (RPMI 1640 medium [Quality Biologicals] containing 10% FBS, 10 mM HEPES, 2 mM glutamine, and antibiotics). Recombinant vaccinia virus stocks were prepared by standard procedures (Earl et al., 1991). Pertussis toxin was obtained from List (Campbell, Calif.). Recombinant chemokines were purchased from Peprotech (Rocky Hill, N.J.). Fura 2-AM and propidium iodide were obtained from Molecular Probes (Eugene, Oreg.). Sodium azide and ATP were from Sigma (St. Louis, Mo.).

CCR5 Contructs. Epitope tagged variants of CCR5 were created to enable detection by the M5 monoclonal antibody (Kodak Rochester, N.Y.). The CCR5 open reading frame was amplified by PCR using the following primers: 1) for full-length CCR5 (designated CCR5): a 3'-oliponucleotide containing (from 3' to 5') 27 bases complementary to the last 9 codons of CCR5, 3 bases for the stop codon, 6 bases for an Xho I restriction site and 8 miscellaneous bases; 2) for CCR5 lacking most of the cytoplasmic C-terminus (designated $CCR5_{306}$): a 3'-oligonucleotide containing (from 3' to 5') 27 bases complementary to codons 298-306 of CCR5, 3 bases for a stop codon, 6 bases for an Xho I restriction site and 8 miscellaneous bases; and 3) for both constructs: a 5'-oligonucleotide containing (from 5' to 3') 8 miscellaneous bases, 6 bases for a Hind III site, 3 bases for the start codon, 24 bases encoding the flag epitope DYKDDDDK (SEQ ID NO: 10) and 27 bases complementary to CCR5 codons 2 to 10. The resulting two PCR products were digested and subcloned between the Hind III and Xho I sites of the changes using a MSIII fluorimeter (Photon Technology International, S. Brunswick, N.J.) in HEK 293 cell lines expressing receptor constructs as previously described. Fuerst, T. R., Niles. E. G. Studier, F. W., and Moss, B. (1986). Briefly, cells were loaded with 2 µM FURA-2 AM at 37° C. for 45 min, washed twice and resuspended at $10^6$ cells/ml in HBSS, pH 7.4. Two ml of the cell suspension were placed in a stirred, water-jacketed cuvette at 37° C. and excited sequentially at 340 and 380 nm. Fluorescence emission was monitored at 510 nm before and after addition of agonists. For some experiments, cells were incubated with 250 ng/ml pertussis toxin for 3 h prior to functional assay.

Cell Fusion Assay. Fusion between effector cells expressing HIV-1 Env and target cells expressing CD4 was quantitated by a vaccinia-based reporter gene assay in which β-galactosidase is produced selectively in fused cells (Nussbaum et al., 1994). As effector cells, HeLa cells were coinfected with vCB-21 R, which encodes the E. Coli LacZ gene under control of the bacteriophage T7 promoter (J. Virol. 70, 5487-5494.), and a recombinant vaccinia virus encoding one of the following HIV-1 Envs (PNAS. 92, 9004-9008.): M-tropic Envs Ba-L (vCB-43; note this is a correction of the nomenclature used for this virus in Broder and Berger, 1995), ADA (vCB-39), SF-162 (vCB-32), and JR-FL (vCB-28); and Unc, an uncleavable mutant of IIIB (vCB-16). In one protocol, the target cells were HEK 293 cell transfectants stably expressing the indicated CCR5 contructs. These cells were coinfected with vTF7-3 encoding T7 RN polymerase (Fuerst et al., 1993) and vCB-3 encoding human CD4 (Cell 85, 1149-12158.). In both viruses the foreign genes are linked to vaccinia early/late promoters; the multiplicity of infection was 10 pfu/cell for each virus. In another protocol, the target cells were NIH 3T3 cells transfected with pcDNA3-based plasmids encoding CCR5 or $CCR5_{306}$ using DOTAP lipofection (Boehringer Mannheim, Indianapolis, Ind.); control cells were transfected with pcDNA3 vector alone. After 4 h incubation in DOTAP at 37° C., cells were coinfected with vTF7-3 and vCB-3; expression of the CCR5 constructs was driven by the T7 promoter. Cell cultures were incubated at 31° C. overnight.

Cell surface expression of CCR5 and $CCR5_{306}$ was analyzed by flow cytometry using as the probe either a rabbit polyclonal antiserum generated against a synthetic peptide representing the predicted extracellular amino terminal domain of CCR5 (amino acids 1-28), or a mAb recognizing the Flag epitope. Specific cell surface staining at comparable intensity was obtained when HEK293 cells stably transfected with either CCR5 or $CCR5_{306}$ were incubated with the anti-CCR5 antiserum. In contrast, cells stably transfected with the closely related receptor CCR2b (75% amino acid identity) gave only background fluorescence equivalent to that observed with the signaling is required for the HIV-1 coreceptor activity of CCR5, using a quantative vaccinia-based reporter gene assay of HIV-1 Env-mediated cell fusion HEK 293 cell transfectants expressing CCR5 or $CCR5_{306}$ (along with vaccinia-encoded CD4) were tested for their ability to fuse with HeLa cells expressing vaccinia-encoded Envs from several M-tropic strains. Comparable levels of fusion occurred with CCR5 and $CCR5_{306}$ for each Env tested. Similar results were obtained in an alternative protocol whereby CCR5 and $CCR5_{306}$ were expressed on NIH 3T3 cells using a transient vaccinia expression system. Thus, the C-terminal truncation that abolished the G protein signal transduction activity of CCR5 had no effect on fusion coreceptor activity.

Pertussis toxin provided an alternative means to test the requirement for G protein signal transduction in the fusion coreceptor activity of CCR5. In the cell fusion assay using the M-tropic Ba-L Env, high concentration of the toxin (500 ng/ml) had no effect on the fusion coreceptor activity of CCR5 expressed transiently in NIH 3T3 cells.

The effects of pertussis toxin were also tested on productive HIV-1 infection, using the Jurkat-derived T cell line PM1 as the target. PM1 cells express CD4 and are highly susceptible to M-tropic HIV-1 strains. Moreover, CCR5 mRNA is expressed in these cells and infection by M-tropic HIV-1 on PM1 cells is CCR5. In the continuous presence of pertussis toxin (500 ng/ml), robust infection by the M-tropic Ba-L isolate in PM1 cells was observed. Consistent with this, when PM1 cells were used as target cells in the cell fusion assay with effector HeLa cells expressing the Ba-L Env, high levels of fusion activity were observed and this was completely resistant to pertussis toxin. Thus, pertussis toxin at concentrations that potently block G protein-mediated signal transduction-had minimal effect on either Env-mediated cell fusion or productive infection. These results parallel earlier reports that pertussis toxin did not process known as receptor sequestration or down modulation. This process is thought to explain in part the phenomenon of receptor desensitization and could be important either for HIV-1 Env-dependent membrane fusion, and/or chemokine inhibition of fusion. CCR5 was strongly downmodulated by cheomkine ligands, whereas the truncated $CCR5_{306}$ receptor was unaffected. This indicates that, in addition to containing critical determinants of signaling, the C-terminal domain of CCR5 also contains critical determinants for chemokine-mediated down-modulation.

It will be apparent to those skilled in the art that various modifications and variations can be made to the compositions and processes of this invention. Thus, it is intended that the present invention cover such modifications and variations, provided they come within the scope of the appended claims and their equivalents.

We claim:

1. A method for identifying a compound which binds to a CCR5 polypeptide, comprising:
   a) incubating components comprising the compound and CCR5 polypeptide under conditions sufficient to allow the components to interact; and
   b) measuring the binding of the compound to CCR5 polypeptide.

2. The method of claim 1, wherein the compound is a peptide.

3. The method of claim 1, wherein the compound is a peptidomimetic.

4. The method of claim 1, wherein the CCR5 polypeptide is expressed in a cell.

5. The method of claim 4 wherein the cell is a recombinant cell line that expresses CCR5 polypeptide.

6. A method for identifying an antibody which binds to a CCR5 polypeptide, comprising:
   incubating components comprising the antibody and CCR5 polypeptide under conditions sufficient to allow the components to interact; and
   measuring the binding of the antibody to CCR5 polypeptide.

7. The method of claim 6, wherein the antibody comprises a polyclonal antibody, monoclonal antibody, or fragment thereof.

8. The method of claim 6, wherein the antibody is specific for an extracellular region of the CCR5 polypeptide.

9. The method of claim 6, wherein the antibody comprises a humanized monoclonal antibody.

* * * * *

UNITED STATES PATENT AND TRADEMARK OFFICE
CERTIFICATE OF CORRECTION

PATENT NO. : 7,374,872 B2
APPLICATION NO. : 11/594375
DATED : May 20, 2008
INVENTOR(S) : Combadiere et al.

It is certified that error appears in the above-identified patent and that said Letters Patent is hereby corrected as shown below:

In the Drawings:
In Figure 2, "Peptide Concetration (µg per ml)" should be --Peptide Concentration (µg per ml)--.

In the Specification:
Column 2, line 20, "40:419428" should be --40:419-428--.

Column 3, line 10, "CCRS" should be --CCR5--.

Column 4, line 23, "strans" should be --strains--.

Column 6, line 24, "polypetide" should be --polypeptide--.

Column 9, line 2, "Strathem" should be --Strathern--.

Column 9, line 21, "the. CCR5" should be --the CCR5--.

Column 9, line 43, "metallothionine" should be --metallothionein--.

Column 9, line 57, "12" should be --1-2--.

Column 9, lines 63-64, "phosplioribosyltranslerase" should be --phosphoribosyltransferase--.

Column 9, line 65, "tk," should read --tk-,--.

Column 9, line 66, "can he" should be --can be--.

Column 10, line 15, "DL-omithine" should be --DL-ornithine--.

Column 13, line 5, "non-functional." should be --non-functional--.

Column 14, line 8, "et al" should be --et al.--.

Column 14, line 12, "With" should be --with--.

Column 14, line 50, "present." should be --present--.

UNITED STATES PATENT AND TRADEMARK OFFICE
CERTIFICATE OF CORRECTION

PATENT NO. : 7,374,872 B2
APPLICATION NO. : 11/594375
DATED : May 20, 2008
INVENTOR(S) : Combadiere et al.

It is certified that error appears in the above-identified patent and that said Letters Patent is hereby corrected as shown below:

Column 14, line 58, "the apeutically" should be --therapeutically--.

Column 16, lines 15-16, "242:423426" should be --242:423-426--.

Column 16, line 17, "1271 77" should be --1271-77--.

Column 17, line 11, "retain." should be --retain--.

Column 17, line 20, "intention" should be --invention--.

Column 17, line 47, "described Merrifield" should be --described in Merrifield--.

Column 17, line 49, "27 62" should be --27-62--.

Column 17, line 50, "0.11.0" should be --0.1-1.0--.

Column 18, line 46, "insure" should be --ensure--.

Column 20, line 14, "beta-galactosidase,a" should be --beta-galactosidase, a--.

Column 22, line 29, "fusion-incompeterit" should be --fusion-incompetent--.

Column 24, line 28, "25889 25897" should be --25889-25897--.

Column 24, line 31, "PROTCOlS" should be --PROTOCOLS--.

Column 24, line 31, "BIOIOLOGY" should be --BIOLOGY--.

Column 24, line 34, "methodology See" should be --methodology. See--.

Column 24, line 39, "invitrogen" should be --Invitrogen--.

Column 25, line 15, "(Invitrogen;San)" should be --Invitrogen, San)--.

Column 26, line 14, "-concentrations" should be --concentrations--.

Column 26, line 51, "composition." should be --composition--.

UNITED STATES PATENT AND TRADEMARK OFFICE
CERTIFICATE OF CORRECTION

PATENT NO. : 7,374,872 B2
APPLICATION NO. : 11/594375
DATED : May 20, 2008
INVENTOR(S) : Combadiere et al.

It is certified that error appears in the above-identified patent and that said Letters Patent is hereby corrected as shown below:

Column 26, line 60, "Sterling.," should be --Sterling,--.

Column 26, line 63, "non-aqueous aqueous" should be --non-aqueous or aqueous--.

Column 27, line 2, "Ringe's" should be --Ringer's--.

Column 27, line 14, "ethyl oleate" should be --ethyloleate--.

Column 27, line 42, "lit is" should be --it is--.

Column 27, line 51, "Scherphofet al." should be --Scherphof et al.--.

Column 27, line 59, "polyethelene" should be --polyethylene--.

Column 28, line 17, "Zelphati et al." should be --Zelphati et al.--.

Column 28, line 29, "MRNA" should be --mRNA--.

Column 29, line 2, "homoygosity" should be --homozygosity--.

Column 29, line 26, "histocormpatibility" should be --histocompatability--.

Column 29, line 41, "cit op." should be --op cit.--.

Column 29, line 44, "from-bp" should be --from bp--.

Column 29, line 53, "matched 15 and" should be --matched and--.

Column 30, line 58, "2 4" should be --2-4--.

Column 31, line 13, "Northein" should be --Northern--.

Column 31, line 61, "CDNA" should be --cDNA--.

Column 31, line 67, "540" should be --5-40--.

Column 33, line 7, "$^{125}$I-MIP1α," should be --$^{125}$I-MIP-1α,--.

UNITED STATES PATENT AND TRADEMARK OFFICE
CERTIFICATE OF CORRECTION

PATENT NO.          : 7,374,872 B2
APPLICATION NO. : 11/594375
DATED                   : May 20, 2008
INVENTOR(S)        : Combadiere et al.

It is certified that error appears in the above-identified patent and that said Letters Patent is hereby corrected as shown below:

Column 33, line 8, "24" should be --2-4--.

Column 33, line 16, "$^{125}$I-MIP-1βbinding" should be --$^{125}$I-MIP-1β binding--.

Column 33, line 22, "competed-2-fold" should be --competed 2-fold--.

Column 33, line 23, "CC CKR1 IC$_{50}$s~100" should be --CC CKR1 (IC$_{50}$~100--.

Column 33, lines 31-32, "MIP-1..alpha." should be --MIP-1α--.

Column 33, line 32, "IC$_{50}$-20" should be --IC$_{50}$~20--.

Column 33, line 61, "polymnerase" should be --polymerase--.

Column 34, line 25, "CCRS" should be --CCR5--.

Column 34, line 54, "CCRS" should be --CCR5--.

Column 35, line 36, "CCRS" should be --CCR5--.

Column 35, line 57, "Fura" should be --FURA--.

Column 35, line 60, "Contructs" should be --Constructs--.

Column 35, line 64, "3'-oliponucleotide" should be --3'-oligonucleotide--.

Column 36, line 15, "Niles. E. G." should be --Niles, E. G.,--.

Column 36, line 29, "*E. Coli* LacZ" should be --*E. coli LacZ*--.

Column 36, line 35, "SF-162" should be --SF162--.

Column 36, line 39, "contructs" should be --constructs--.

Column 36, line 64, "is required" should be deleted.

UNITED STATES PATENT AND TRADEMARK OFFICE
CERTIFICATE OF CORRECTION

PATENT NO. : 7,374,872 B2
APPLICATION NO. : 11/594375
DATED : May 20, 2008
INVENTOR(S) : Combadiere et al.

It is certified that error appears in the above-identified patent and that said Letters Patent is hereby corrected as shown below:

Column 36, line 66, "fusion" should be --fusion.--.

Column 38, line 6, "transduction-had" should be --transduction had--.

Column 38, line 14, "cheomkine" should be --chemokine--.

Signed and Sealed this

Thirteenth Day of January, 2009

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 1225
<212> TYPE: DNA
<213> ORGANISM: Homo sapiens
<220> FEATURE:
<221> NAME/KEY: CDS
<222> LOCATION: (27)..(1082)

<400> SEQUENCE: 1
aagaaactct ccccgggtgg aacaag atg gat tat caa gtg tca agt cca atc       53
                              Met Asp Tyr Gln Val Ser Ser Pro Ile
                                1               5 tat gac atc aat tat tat aca tcg gag ccc tgc caa aaa atc aat gtg      101
Tyr Asp Ile Asn Tyr Tyr Thr Ser Glu Pro Cys Gln Lys Ile Asn Val
 10                  15                  20                  25 aag caa atc gca gcc cgc ctc ctg cct ccg ctc tac tca ctg gtg ttc      149
Lys Gln Ile Ala Ala Arg Leu Leu Pro Pro Leu Tyr Ser Leu Val Phe
                 30                  35                  40 atc ttt ggt ttt gtg ggc aac atg ctg gtc atc ctc atc ctg ata aac      197
Ile Phe Gly Phe Val Gly Asn Met Leu Val Ile Leu Ile Leu Ile Asn
             45                  50                  55 tgc aaa agg ctg aag agc atg act gac atc tac ctg ctc aac ctg gcc      245
Cys Lys Arg Leu Lys Ser Met Thr Asp Ile Tyr Leu Leu Asn Leu Ala
         60                  65                  70 atc tct gac ctg ttt ttc ctt ctt act gtc ccc ttc tgg gct cac tac      293
Ile Ser Asp Leu Phe Phe Leu Leu Thr Val Pro Phe Trp Ala His Tyr
     75                  80                  85 ttg gcc gcc cag tgg gac ttt gga aat aca atg tgt caa ctc ttg aca      341
Leu Ala Ala Gln Trp Asp Phe Gly Asn Thr Met Cys Gln Leu Leu Thr
 90                  95                 100                 105 ggg ctc tat ttt ata ggc ttc ttc tct gga atc ttc ttc atc atc ctc      389
Gly Leu Tyr Phe Ile Gly Phe Phe Ser Gly Ile Phe Phe Ile Ile Leu
                110                 115                 120 ctg aca atc gat agg tac ctg gct gtc gtc cat gct gtg ttt gct tta      437
```

-continued

| | | |
|---|---|---|
| aaa gcc agg acg gtc acc ttt ggg gtg gta aca agt gtg atc act tgg<br>Lys Ala Arg Thr Val Thr Phe Gly Val Val Thr Ser Val Ile Thr Trp<br>       140                    145                    150 | 485 |

Leu Thr Ile Asp Arg Tyr Leu Ala Val Val His Ala Val Phe Ala Leu
       125                    130                    135 aaa gcc agg acg gtc acc ttt ggg gtg gta aca agt gtg atc act tgg     485
Lys Ala Arg Thr Val Thr Phe Gly Val Val Thr Ser Val Ile Thr Trp
       140                    145                    150 gtg gtg gct gtg ttt gcg tct ctc cca gga atc atc ttt acc aga tct     533
Val Val Ala Val Phe Ala Ser Leu Pro Gly Ile Ile Phe Thr Arg Ser
       155                    160                   165 caa aaa gaa ggt ctt cat tac acc tgc agc tct cat ttt cca tac agt     581
Gln Lys Glu Gly Leu His Tyr Thr Cys Ser Ser His Phe Pro Tyr Ser
170                        175                    180                   185 cag tat caa ttc tgg aag aat ttc cag aca tta aag ata gtc atc ttg     629
Gln Tyr Gln Phe Trp Lys Asn Phe Gln Thr Leu Lys Ile Val Ile Leu
                      190                    195                   200 ggg ctg gtc ctg ccg ctg ctt gtc atg gtc atc tgc tac tcg gga atc     677
Gly Leu Val Leu Pro Leu Leu Val Met Val Ile Cys Tyr Ser Gly Ile
                      205                    210                   215 cta aaa act ctg ctt cgg tgt cga aat gag aag aag agg cac agg gct     725
Leu Lys Thr Leu Leu Arg Cys Arg Asn Glu Lys Lys Arg His Arg Ala
                      220                    225                   230 gtg agg ctt atc ttc acc atc atg att gtt tat ttt ctc ttc tgg gct     773
Val Arg Leu Ile Phe Thr Ile Met Ile Val Tyr Phe Leu Phe Trp Ala
235                      240                    245 ccc tac aac att gtc ctt ctc ctg aac acc ttc agg gaa ttc ttt ggc     821
Pro Tyr Asn Ile Val Leu Leu Leu Asn Thr Phe Gln Glu Phe Phe Gly
250                      255                    260                   265 ctg aat aat tgc agt agc tct aac agg ttg gac caa gct atg cag gtg     869
Leu Asn Asn Cys Ser Ser Ser Asn Arg Leu Asp Gln Ala Met Gln Val
                      270                    275                   280 aca gag act ctt ggg atg acg cac tgc tgc atc aac ccc atc atc tat     917
Thr Glu Thr Leu Gly Met Thr His Cys Cys Ile Asn Pro Ile Ile Tyr
                      285                    290                   295 gcc ttt gtc ggg gag aag ttc aga aac tac ctc tta gtc ttc ttc caa     965
Ala Phe Val Gly Glu Lys Phe Arg Asn Tyr Leu Leu Val Phe Phe Gln
                      300                    305                   310 aag cac att gcc aaa cgc ttc tgc aaa tgc tgt tct att ttc agc aa     1013
Lys His Ile Ala Lys Arg Phe Cys Lys Cys Cys Ser Ile Phe Gln Gln
315                      320                    325 gag gct ccc gag cga gca agc tca gtt tac acc cga tcc act ggg gag   1061
Glu Ala Pro Glu Arg Ala Ser Ser Val Tyr Thr Arg Ser Thr Gly Glu
330                      335                    340                   345 cag gaa ata tct gtg ggc ttg tgacacggac tcaagtgggc tggtgaccca     1112
Gln Glu Ile Ser Val Gly Leu
                      350 gtcagagttg tgcacatggc ttagttttca tacacagcct gggctggggg tggggtggga    1172 gaggtctttt ttaaaaggaa gttactgtta tagagggtct aagattcatc cat            1225

<210> SEQ ID NO 2
<211> LENGTH: 352
<212> TYPE: PRT
<213> ORGANISM: Homo sapiens

<400> SEQUENCE: 2

Met Asp Tyr Gln Val Ser Ser Pro Ile Tyr Asp Ile Asn Tyr Tyr Thr
1                 5                   10                 15

Ser Glu Pro Cys Gln Lys Ile Asn Val Lys Gln Ile Ala Ala Arg Leu
                 20                  25                 30

Leu Pro Pro Leu Tyr Ser Leu Val Phe Ile Phe Gly Phe Val Gly Asn
        35                  40                 45

```
Met Leu Val Ile Leu Ile Leu Ile Asn Cys Lys Arg Leu Lys Ser Met
 50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Leu Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

<210> SEQ ID NO 3
<211> LENGTH: 1225
<212> TYPE: DNA
<213> ORGANISM: Homo sapiens
<220> FEATURE:
<221> NAME/KEY: CDS
<222> LOCATION: (27)..(1082)

<400> SEQUENCE: 3

```
aagaaactct ccccgggtgg aacaag atg gat tat caa gtg tca agt cca atc      53
                             Met Asp Tyr Gln Val Ser Ser Pro Ile
                               1               5 tat gac atc aat tat tat aca tcg gag ccc tgc caa aaa atc aat gtg     101
Tyr Asp Ile Asn Tyr Tyr Thr Ser Glu Pro Cys Gln Lys Ile Asn Val
 10                  15                  20                  25 aag caa atc gca gcc cgc ctc ctg cct ccg ctc tac tca ctg gtg ttc     149
Lys Gln Ile Ala Ala Arg Leu Leu Pro Pro Leu Tyr Ser Leu Val Phe
```

-continued

```
                  30                    35                    40
atc ttt ggt ttt gtg ggc aac atg ctg gtc atc ctc atc ctg ata aac      197
Ile Phe Gly Phe Val Gly Asn Met Leu Val Ile Leu Ile Leu Ile Asn
             45                    50                    55 tgc aaa agg ctg aag agc atg act gac atc tac ctg ctc aac ctg gcc      245
Cys Lys Arg Leu Lys Ser Met Thr Asp Ile Tyr Leu Leu Asn Leu Ala
         60                    65                    70 atc tct gac ctg ttt ttc ctt ctt act gtc ccc ttc tgg gct cac tat      293
Ile Ser Asp Leu Phe Phe Leu Leu Thr Val Pro Phe Trp Ala His Tyr
     75                    80                    85 gct gcc gcc cag tgg gac ttt gga aat aca atg tgt caa ctc ttg aca      341
Ala Ala Ala Gln Trp Asp Phe Gly Asn Thr Met Cys Gln Leu Leu Thr
 90                    95                   100                   105 ggg ctc tat ttt ata ggc ttc ttc tct gga atc ttc ttc atc atc ctc      389
Gly Leu Tyr Phe Ile Gly Phe Phe Ser Gly Ile Phe Phe Ile Ile Leu
                    110                   115                   120 ctg aca atc gat agg tac ctg gct gtc gtc cat gct gtg ttt gct tta      437
Leu Thr Ile Asp Arg Tyr Leu Ala Val Val His Ala Val Phe Ala Leu
                125                   130                   135 aaa gcc agg acg gtc acc ttt ggg gtg gtg aca agt gtg atc act tgg      485
Lys Ala Arg Thr Val Thr Phe Gly Val Val Thr Ser Val Ile Thr Trp
            140                   145                   150 gtg gtg gct gtg ttt gcg tct ctc cca gga atc atc ttt acc aga tct      533
Val Val Ala Val Phe Ala Ser Leu Pro Gly Ile Ile Phe Thr Arg Ser
        155                   160                   165 caa aaa gaa ggt ctt cat tac acc tgc agc tct cat ttt cca tac agt      581
Gln Lys Glu Gly Leu His Tyr Thr Cys Ser Ser His Phe Pro Tyr Ser
170                   175                   180                   185 cag tat caa ttc tgg aag aat ttc cag aca tta aag ata gtc atc ttg      629
Gln Tyr Gln Phe Trp Lys Asn Phe Gln Thr Leu Lys Ile Val Ile Leu
                    190                   195                   200 ggg ctg gtc ctg ccg ctg ctt gtc atg gtc atc tgc tac tcg gga atc      677
Gly Leu Val Leu Pro Leu Leu Val Met Val Ile Cys Tyr Ser Gly Ile
                205                   210                   215 cta aaa act ctg ctt cgg tgt cga aat gag aag aag agg cac agg gct      725
Leu Lys Thr Leu Leu Arg Cys Arg Asn Glu Lys Lys Arg His Arg Ala
            220                   225                   230 gtg agg ctt atc ttc acc atc atg att gtt tat ttt ctc ttc tgg gct      773
Val Arg Leu Ile Phe Thr Ile Met Ile Val Tyr Phe Leu Phe Trp Ala
        235                   240                   245 ccc tac aac att gtc ctt ctc ctg aac acc ttc cag gaa ttc ttt ggc      821
Pro Tyr Asn Ile Val Leu Leu Leu Asn Thr Phe Gln Glu Phe Phe Gly
250                   255                   260                   265 ctg aat aat tgc agt agc tct aac agg ttg gac caa gct atg cag gtg      869
Leu Asn Asn Cys Ser Ser Ser Asn Arg Leu Asp Gln Ala Met Gln Val
                    270                   275                   280 aca gag act ctt ggg atg acg cac tgc tgc atc aac ccc atc atc tat      917
Thr Glu Thr Leu Gly Met Thr His Cys Cys Ile Asn Pro Ile Ile Tyr
                285                   290                   295 gcc ttt gtc ggg gag aag ttc aga aac tac ctc tta gtc ttc ttc caa      965
Ala Phe Val Gly Glu Lys Phe Arg Asn Tyr Leu Leu Val Phe Phe Gln
            300                   305                   310 aag cac att gcc aaa cgc ttc tgc aaa tgc tgt tct att ttc cag caa     1013
Lys His Ile Ala Lys Arg Phe Cys Lys Cys Cys Ser Ile Phe Gln Gln
        315                   320                   325 gag gct ccc gag cga gca agc tca gtt tac acc cga tcc act ggg gag     1061
Glu Ala Pro Glu Arg Ala Ser Ser Val Tyr Thr Arg Ser Thr Gly Glu
330                   335                   340                   345 cag gaa ata tct gtg ggc ttg tgacacggac tcaagtgggc tggtgaccca        1112
Gln Glu Ile Ser Val Gly Leu
```

Gln Glu Ile Ser Val Gly Leu
              350 gtcagagttg tgcacatggc ttagttttca tacacagcct gggctggggg tggggtggga        1172 gaggtctttt ttaaaaggaa gttactgtta tagagggtct aagattcatc cat              1225

<210> SEQ ID NO 4
<211> LENGTH: 352
<212> TYPE: PRT
<213> ORGANISM: Homo sapiens

<400> SEQUENCE: 4

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu

```
                      340              345              350

<210> SEQ ID NO 5
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is Ala or Leu

<400> SEQUENCE: 5

Xaa Ala Ala Gln Trp Asp Phe Gly Asn Thr Met Cys
1               5                   10

<210> SEQ ID NO 6
<211> LENGTH: 24
<212> TYPE: PRT
<213> ORGANISM: Homo sapiens

<400> SEQUENCE: 6

Arg Ser Gln Lys Glu Gly Leu His Tyr Thr Cys Ser Ser His Phe Pro
1               5                   10                  15

Tyr Ser Gln Tyr Gln Phe Trp Lys
            20

<210> SEQ ID NO 7
<211> LENGTH: 16
<212> TYPE: PRT
<213> ORGANISM: Homo sapiens

<400> SEQUENCE: 7

Gln Glu Phe Phe Gly Leu Asn Asn Cys Ser Ser Ser Asn Arg Leu Asp
1               5                   10                  15

<210> SEQ ID NO 8
<211> LENGTH: 360
<212> TYPE: PRT
<213> ORGANISM: Homo sapiens

<400> SEQUENCE: 8

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
        50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160
```

```
Ser Val Ile Thr Trp Leu Val Ala Val Phe Ala Ser Val Pro Gly Ile
            165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
            195                 200                 205

Leu Gly Leu Val Leu Pro Leu Ile Met Val Ile Cys Tyr Ser Gly
            210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
            245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
            275                 280                 285

Val Thr Glu Thr Leu Gly Met Thr His Cys Cys Ile Asn Pro Ile Ile
            290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
            325                 330                 335

Arg Glu Thr Val Asp Gly Val Thr Ser Thr Asn Thr Pro Ser Thr Gly
            340                 345                 350

Glu Gln Glu Val Ser Ala Gly Leu
            355                 360

<210> SEQ ID NO 9
<211> LENGTH: 355
<212> TYPE: PRT
<213> ORGANISM: Homo sapiens

<400> SEQUENCE: 9

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
            35                  40                  45

Leu Val Gly Asn Ile Leu Val Val Leu Val Leu Val Gln Tyr Lys Arg
        50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
            85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
            115                 120                 125

Ile Asp Arg Tyr Leu Ala Ile Val His Ala Val Phe Ala Leu Arg Ala
            130                 135                 140

Arg Thr Val Thr Phe Gly Val Ile Thr Ser Ile Ile Trp Ala Leu
145                 150                 155                 160

Ala Ile Leu Ala Ser Met Pro Gly Leu Tyr Phe Ser Lys Thr Gln Trp
```

```
                         165                 170                 175
Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
            195                 200                 205

Val Leu Pro Leu Leu Val Met Ile Ile Cys Tyr Thr Gly Ile Ile Lys
            210                 215                 220

Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
            245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
            275                 280                 285

Ile Ala Tyr Thr His Cys Cys Val Asn Pro Val Ile Tyr Ala Phe Val
            290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
            325                 330                 335

Glu Arg Val Ser Ser Thr Ser Pro Ser Thr Gly Glu His Glu Leu Ser
            340                 345                 350

Ala Gly Phe
        355

<210> SEQ ID NO 10
<211> LENGTH: 8
<212> TYPE: PRT
<213> ORGANISM: Artificial
<220> FEATURE:
<223> OTHER INFORMATION: FLAG epitope

<400> SEQUENCE: 10

Asp Tyr Lys Asp Asp Asp Asp Lys
1               5
```